(12) United States Patent
Kirkpatrick et al.

(10) Patent No.: US 7,858,657 B2
(45) Date of Patent: Dec. 28, 2010

(54) WORTMANNIN ANALOGS AND METHODS OF USING SAME IN COMBINATION WITH CHEMOTHERAPEUTIC AGENTS

(75) Inventors: Lynn D. Kirkpatrick, Houston, TX (US); Garth Powis, Houston, TX (US); Peter Wipf, Pittsburgh, PA (US)

(73) Assignees: Proix Pharmaceutical Corp., Seattle, WA (US); Arizona Board of Regents, Acting on Behalf of The University of Arizona, Tucson, AZ (US); University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 12/235,730

(22) Filed: Sep. 23, 2008

(65) Prior Publication Data

US 2009/0087441 A1  Apr. 2, 2009

Related U.S. Application Data

(63) Continuation of application No. 11/178,553, filed on Jul. 11, 2005, now Pat. No. 7,446,124.

(60) Provisional application No. 60/586,687, filed on Jul. 9, 2004.

(51) Int. Cl.
*A61K 31/352* (2006.01)
*A61K 31/4025* (2006.01)
*C07D 311/78* (2006.01)
*C07D 405/14* (2006.01)

(52) U.S. Cl. .................. 514/422; 514/453; 548/525; 549/276

(58) Field of Classification Search .................. 514/422, 514/543; 549/383, 276; 548/525
See application file for complete search history.

(56) References Cited

U.S. PATENT DOCUMENTS

| | | | |
|---|---|---|---|
| 3,668,222 | A | 6/1972 | Hauser |
| 4,636,195 | A | 1/1987 | Wolinsky |
| 5,480,906 | A | 1/1996 | Creemer et al. |
| 5,602,278 | A | 2/1997 | Kirkpatrick |
| 6,703,414 | B2 | 3/2004 | Powis et al. |
| 7,081,475 | B2 | 7/2006 | Powis et al. |
| 7,446,124 | B2 | 11/2008 | Kirkpatrick et al. |
| 2003/0109572 | A1 | 6/2003 | Powis |
| 2006/0063824 | A1 | 3/2006 | Kirkpatrick et al. |
| 2006/0128793 | A1 | 6/2006 | Zask et al. |
| 2006/0167080 | A1 | 7/2006 | Powis et al. |

FOREIGN PATENT DOCUMENTS

| | | | |
|---|---|---|---|
| EP | 0658343 | A1 | 6/1995 |
| EP | 1435941 | B1 | 8/2006 |
| EP | 1686124 | A1 | 8/2006 |
| GB | 2 302 021 | A * | 1/1997 |
| GB | 2302021 | A | 1/1997 |
| WO | WO 90/01969 | A1 | 3/1990 |
| WO | WO 90/03768 | A1 | 4/1990 |
| WO | WO 03/024183 | A2 | 3/2003 |
| WO | WO 2006/044453 | A1 | 4/2006 |
| WO | WO 2007/008200 | A1 | 1/2007 |

OTHER PUBLICATIONS

Wipf et al., Org. Biomol. Chem. (2004), vol. 2, pp. 1911-1920 (published on the Web Jun. 14, 2004).*
Norman et al., J. Med. Chem. (1996), vol. 39, pp. 1106-1111.*
Submitted to applicant in parent U.S. Appl. No. 11/178,553.*
Ciardiello et al. Epidermal Growth Factor Receptor Tyrosine Kinase Inhibitors in Late Stage Clinical Trials, 2003, Expert Opinion on Emerging Drugs, 8(2):501-514.
Sorensen et al, Paclitaxel, Gemcitabine, and Cisplatin in Non-resectable Non-small-cell Lung Cancer, 1999, Annals of Oncology, 10(9):1043-1049.
Kirkpatrick et al. Antitumor Activity, Pharmacodynamics and Toxicity of PX-866 a Novel Inhibitor of Phosphoinositide-3-kinase, 2004, European Journal of Cancer, 2(8): 77.
Ihle et al. Molecular Pharmacology and Antitumor Activity of PX-866, a Novel Inhibitor of Phosphoinositide-3-kinase Signaling, 2004, Molecular Cancer Therapeutics, 3(7):763-772.
Brevis et al., Faranoxi-A New Antitumor Agent, 1996, J. Chemo. 8(1):67-69.
Zalgeviciene et al., Embryotoxicity and Teratogenicity of Some Derivatives of Chloroethylaminophenylacetic Acid, 1998, Pathology Oncol. Res. 4(1):27-29.
Haefliger et al., Selektive Funktionalisierung von Wortmannin mit Hilfe einer Furanring-Maskierung, 1975, Helvetia Chimica Acta 58(6):Nr. 179-180, pp. 1620-1628.
Norman et al., Studies on the Mechanism of Phosphatidylinositol 3-Kinase Inhibition by Wortmannin and Related Analogs, 1996, J. Med. Chem. 39:1106-1111.
Langer, New Methods of Drug Delivery, 1990, Science 249:1527-1533.
Mathiowitz et al., Photochemical Rupture of Microcapsules: A Model System, 1981, J. App. Poly. Sci. 26:809-822.
Kohn, Current Trends in the Development of Synthetic Materials for Medical Applications, 1990, Pharmaceutical Technology, 14(10):32-41.
Folch et al., A Simple Method for the Isolation and Purification of Total Lipides from Animal Tissues, 1957, J. Biol. Chem. 226:497-509.
Clarke et al., Alkaline O→N-transacylation: A New Method for the Quantitative Deacylation of Phospholipids, 1981, BioChem. J. 195:301-306.
Auger et al., Separation of Novel Polyphosphoinositides, 1990, Methods in Inositide Research, pp. 159-166, Irvine ed., Raven Press Ltd., New York, NY.
Lala et al., Role of Nitric and Oxide in Tumor Progression: Lessons from Experimental Tumors, 1998, Cancer and Metastasis Reviews 17(1):91-106.

(Continued)

*Primary Examiner*—Taofiq A Solola
(74) *Attorney, Agent, or Firm*—Wilson Sonsini Goodrich & Rosati

(57) ABSTRACT

Novel wortmannin analogs and their use in inhibiting PI-3-kinase activity in mammals and the treatment or prevention of cancer and tumor formation in a subject are described herein. Preferably, the wortmannin analogs may be administered with other chemotherapeutic agents in the treatment of cancer.

8 Claims, 18 Drawing Sheets

OTHER PUBLICATIONS

Golub et al., Molecular Classification of Cancer: Class Discovery and Class Prediction by Gene Expression Monitoring, 1999, Science 286:531-537.

Wipf et al., Synthesis and Biological Evaluation of Synthetic Viridins Derived from C(20)-Heteroalkylation of the Steroidal PI-3-Kinase Inhibitor Wortmannin, 2004, Org. Biomol. Chem. 2:1911-1920.

* cited by examiner

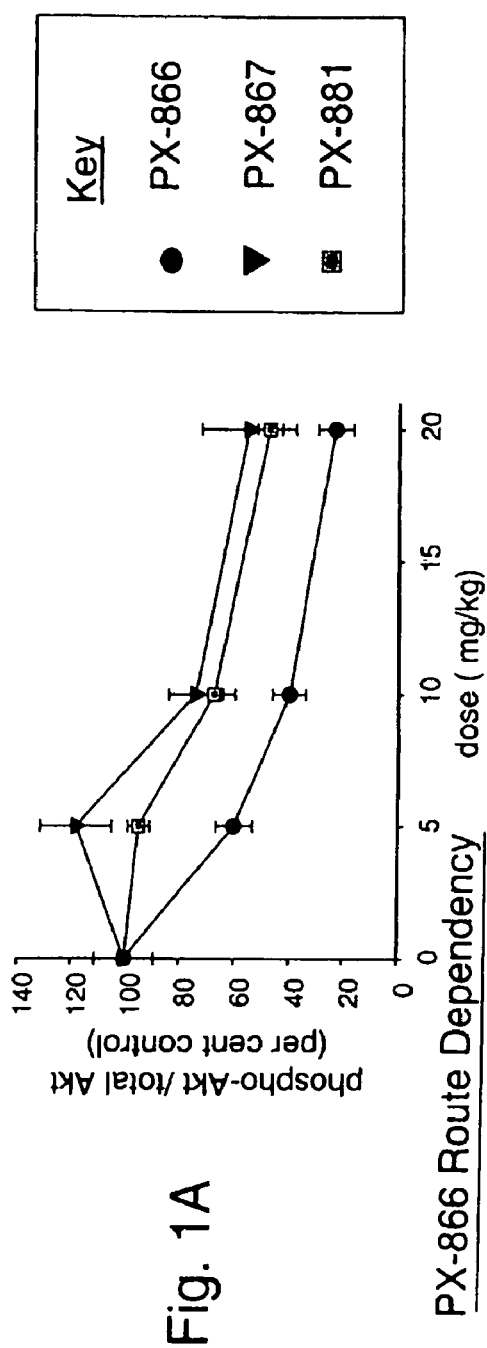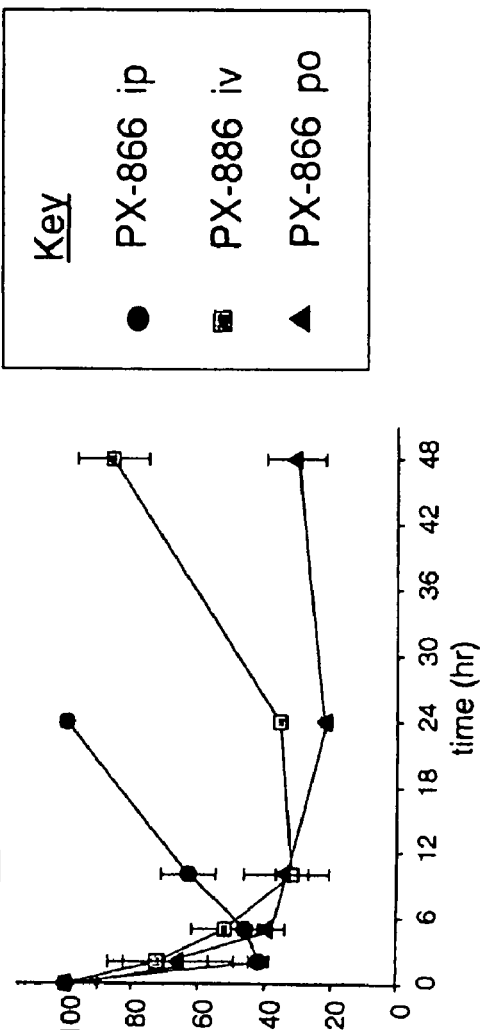
Fig. 1A Dose Dependency
Fig. 1B PX-866 Route Dependency
Inhibition of HT-29 xenograft phospho-Akt

Scheduling of PX-866 before and after Iressa
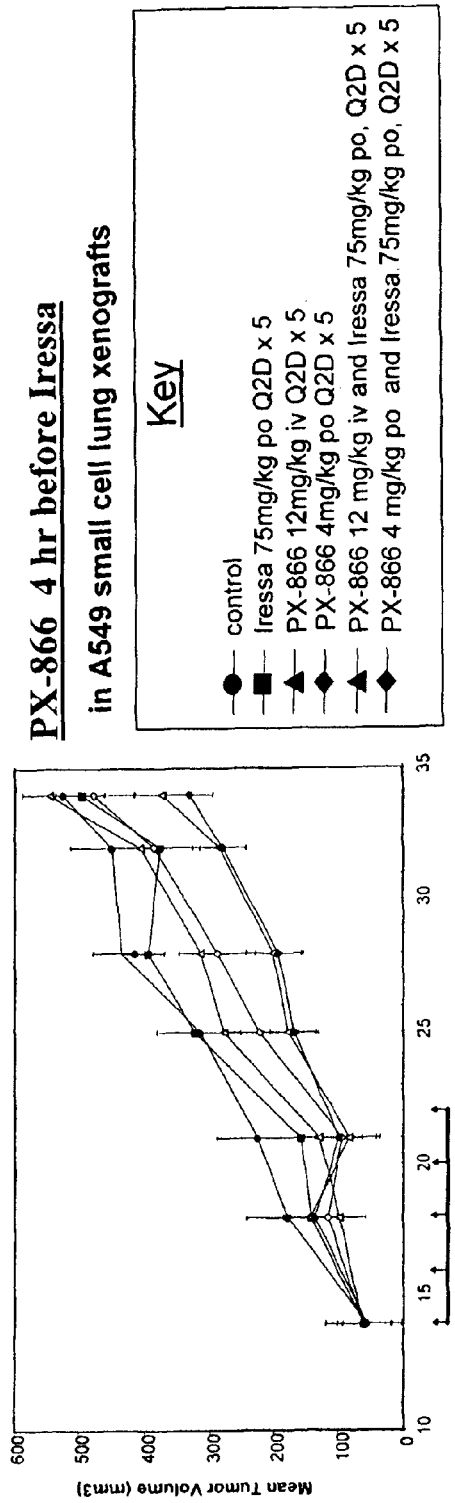
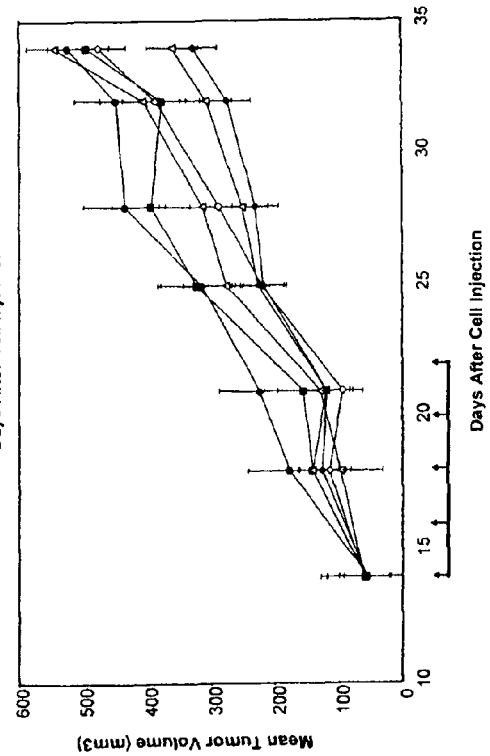
Fig. 11A — PX-866 4 hr before Iressa in A549 small cell lung xenografts
Fig. 11B — PX-866 24 hr after Iressa in A549 small cell lung xenografts
Key:
- control
- Iressa 75mg/kg po Q2D x 5
- PX-866 12mg/kg iv Q2D x 5
- PX-866 4mg/kg po Q2D x 5
- PX-866 12 mg/kg iv and Iressa 75mg/kg po, Q2D x 5
- PX-866 4 mg/kg po and Iressa 75mg/kg po, Q2D x 5
(8 mice per group)
↑ shows Iressa administration

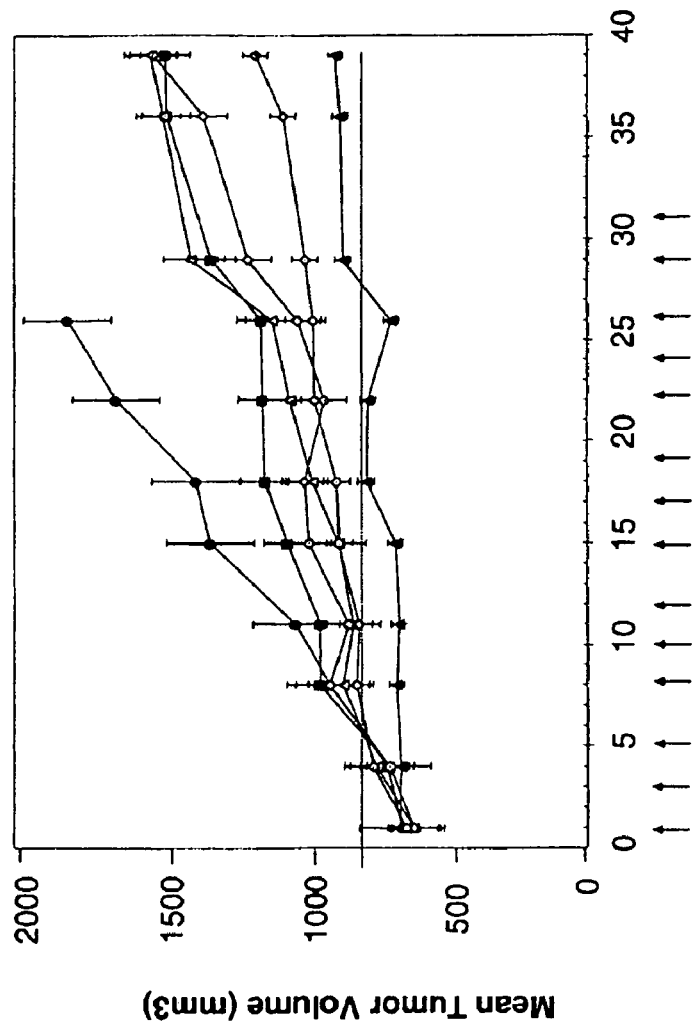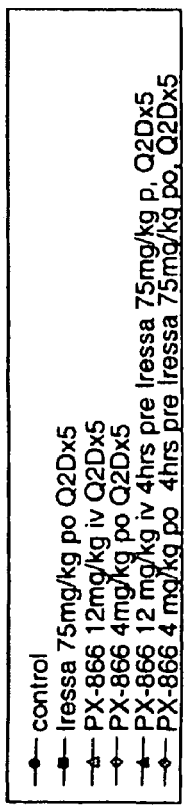
Fig. 12

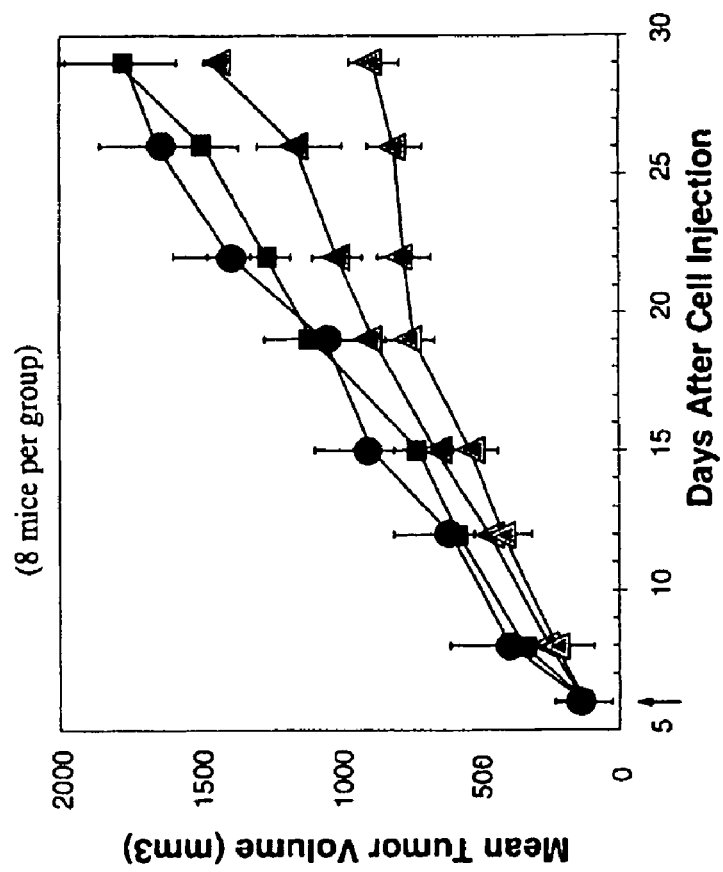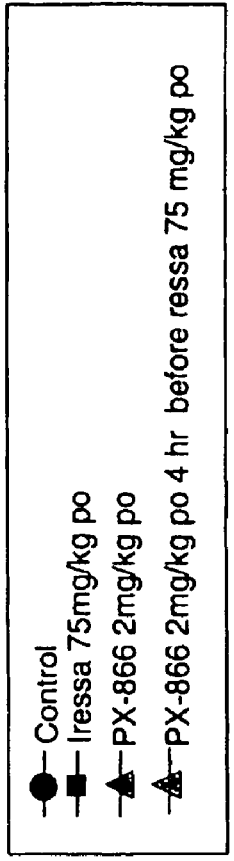
Fig. 13

Fig. 16B
DJM2-170
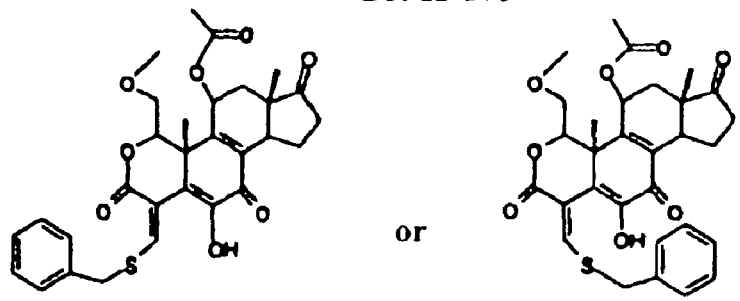
or
DJM2-171
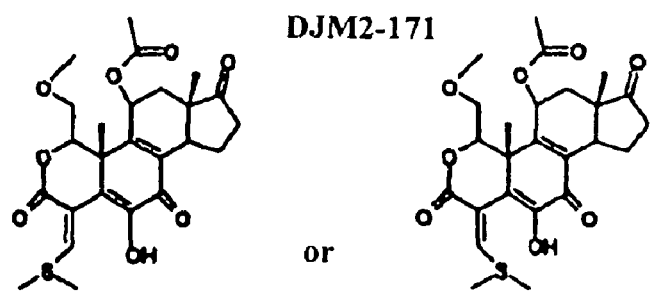
or
DJM2-177
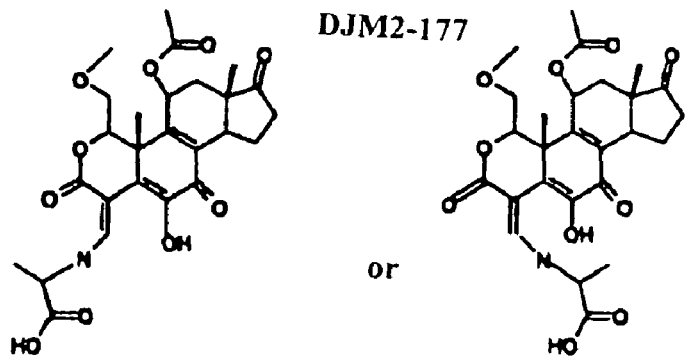
or
DJM2-181
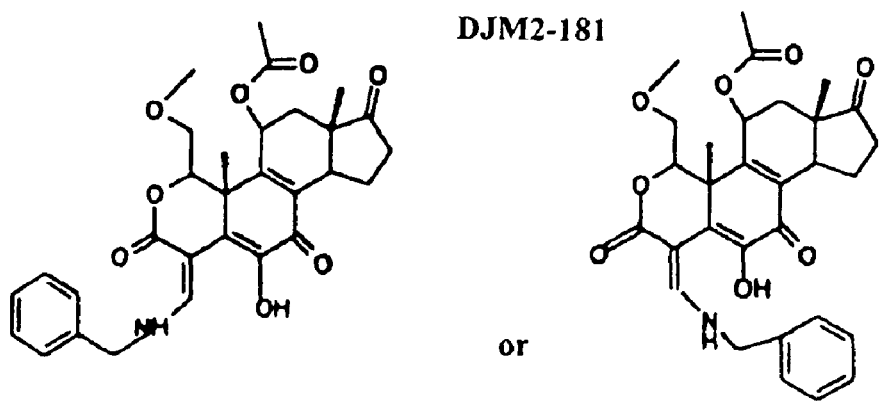
or

US 7,858,657 B2

WORTMANNIN ANALOGS AND METHODS OF USING SAME IN COMBINATION WITH CHEMOTHERAPEUTIC AGENTS

CROSS REFERENCE TO RELATED APPLICATIONS

This application is a continuation of and claims priority from U.S. patent application Ser. No. 11/178,553 filed Jul. 11, 2005, now U.S. Pat. No. 7,446,124, which claims priority to U.S. Provisional Application No. 60/586,687 filed Jul. 9, 2004; both applications are incorporated herein by reference in its entirety.

BACKGROUND OF THE INVENTION

The present invention relates to wortmannin analogs, and methods of using these derivatives alone or in combination with chemotherapeutic agents to inhibit PI-3-kinase activity and to treat certain malignant tumors and other cancers. Wortmannin is a known potent inhibitor of phosphotidylinositol-3-kinase (PI-3-kinase) and anti-cancer agent. Wortmannin is a naturally occurring compound isolated from culture broths of the fungus Penicillium wortmannin and has the basic structure shown in U.S. Pat. No. 5,480,906, which is incorporated herein by reference.

SUMMARY OF THE INVENTION

One aspect of the present invention provides novel wortmannin analogs and methods of inhibiting cancer in a subject comprising administering to a subject a pharmaceutically effective dose of a wortmannin analog.

Another aspect of the present invention provides for a method of inhibiting PI-3-kinase activity in mammals by administering an effective amount of a wortmannin analog.

Another aspect of the present invention provides for use of the compounds as anti-cancer (anti-tumor) agents, and also for pharmaceutical formulations that includes the compound in combination with a pharmaceutically acceptable carrier, recipient or diluent.

A further aspect of the present invention provides for the use of wortmannin analogs in combination with chemotherapeutic agents to treat cancer.

BRIEF DESCRIPTION OF THE DRAWINGS

For a fuller understanding of the nature and advantages of the present invention, reference should be had to the following detailed description taken in connection with the accompanying drawings, in which:

FIG. 1A is a graph of the dose dependency of percent control of HT-29 xenograft phospho-Akt by wortmannin analogs of the present invention. FIG. 1B is a graph of the route dependency of the percent control of HT-29 xenograft phosphor-Akt by the wortmannin analog PX-866 of the present invention.

FIG. 11A is a graph of the mean tumor volume (in $mm^3$) following treatment with PX-866, a wortmannin analog of the present invention, and Iressa four hours later in A549 small cell lung xenografts. FIG. 11B is a graph of the mean tumor volume (in $mm^3$) following treatment with PX-866, a wortmannin analog of the present invention, in combination with Iressa in A549 small cell lung xenografts.

FIG. 12 is a graph of the mean tumor volume (in $mm^3$) following treatment with PX-866, a wortmannin analog of the present invention, alone or prior to administration of Iressa in A549 Human Lung Tumor Xenografts.

FIG. 13 is a graph of the mean tumor volume (in $mm^3$) following treatment with PX-866, a wortmannin analog of the present invention, alone or prior to administration of Iressa in HT-29 colon cancer cells.

DETAILED DESCRIPTION OF THE INVENTION

Figure 2:
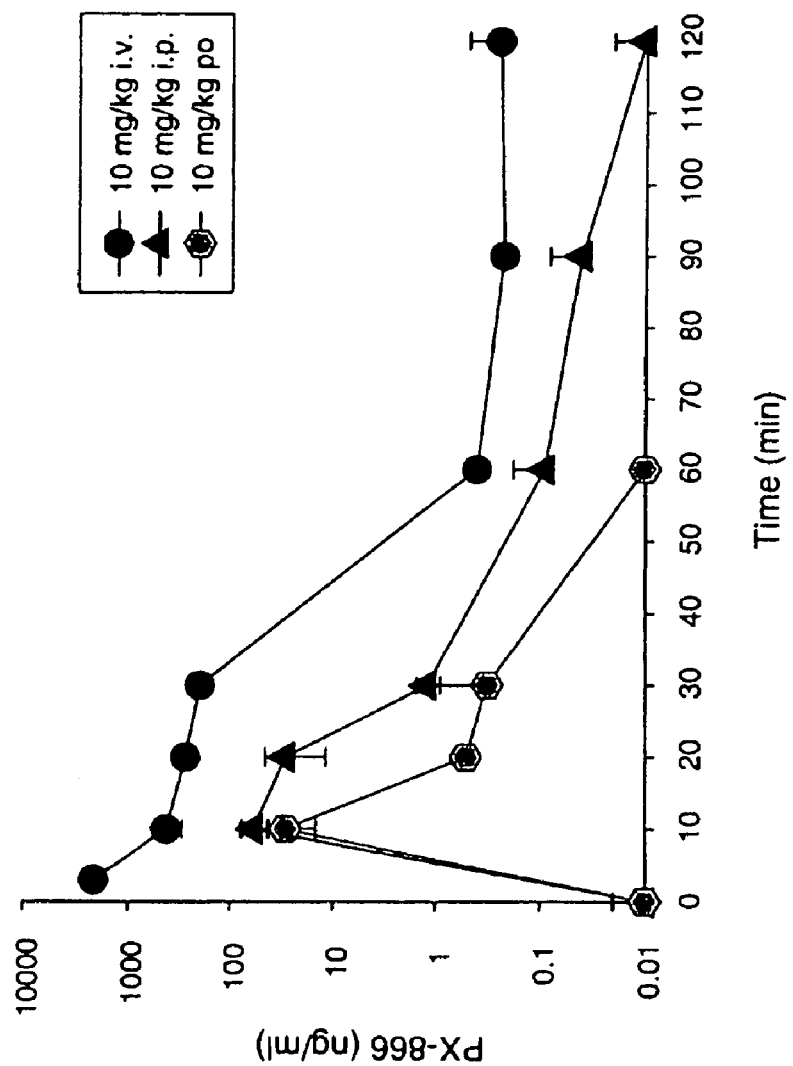
FIG. 2 is a graph of the concentration of PX-866 (in ng/ml) in mouse plasma following intravenous, intraperitoneal and oral administration.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "fibroblast" is a reference to one or more fibroblasts and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

The methods as described herein for use contemplate prophylactic use as well as curative use in therapy of an existing condition. As used herein, the term "about" means plus or minus 10% of the numerical value of the number with which it is being used. Therefore, about 50% means in the range of 45%-55%.

"Administering" when used in conjunction with a therapeutic means to administer a therapeutic systemically or locally, such as directly into or onto a target tissue, or to administer a therapeutic to a patient whereby the therapeutic positively impacts the tissue to which it is targeted. Thus, as used herein, the term "administering", when used in conjunction with a wortmannin analog, can include, but is not limited to, providing a wortmannin analog into or onto the target tissue; providing a wortmannin analog systemically to a patient by, e.g., intravenous injection whereby the therapeutic reaches the target tissue or cells. "Administering" a composition may be accomplished by injection, topical administration, oral administration or by other methods alone or in combination with other known techniques. Such combination techniques include heating, radiation and ultrasound.

As used herein, the term "therapeutic" means an agent utilized to treat, combat, ameliorate, prevent or improve an unwanted condition or disease of a patient. In part, embodiments of the present invention are directed to the treatment of cancer and/or the amelioration of the symptoms of cancer.

A "therapeutically effective amount" or "effective amount" of a composition is a predetermined amount calculated to achieve the desired effect, i.e., inhibiting, blocking, or reversing the activation, migration, or proliferation of cells or to effectively treat cancer or ameliorate the symptoms of cancer. A therapeutically effective amount of a wortmannin analog of this invention is typically an amount such that when it is administered in a physiologically tolerable excipient composition, it is sufficient to achieve an effective concentration in the plasma or serum or an effective local concentration in a target tissue. Effective amounts of compounds of the present invention can be measured by improvements in tumor size, tumor burden or symptoms experienced by the patient being treated. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated.

The term "inhibiting" includes the administration of a compound of the present invention to prevent the onset of the symptoms, alleviating the symptoms, or eliminating the disease, condition or disorder.

Figure 16A:
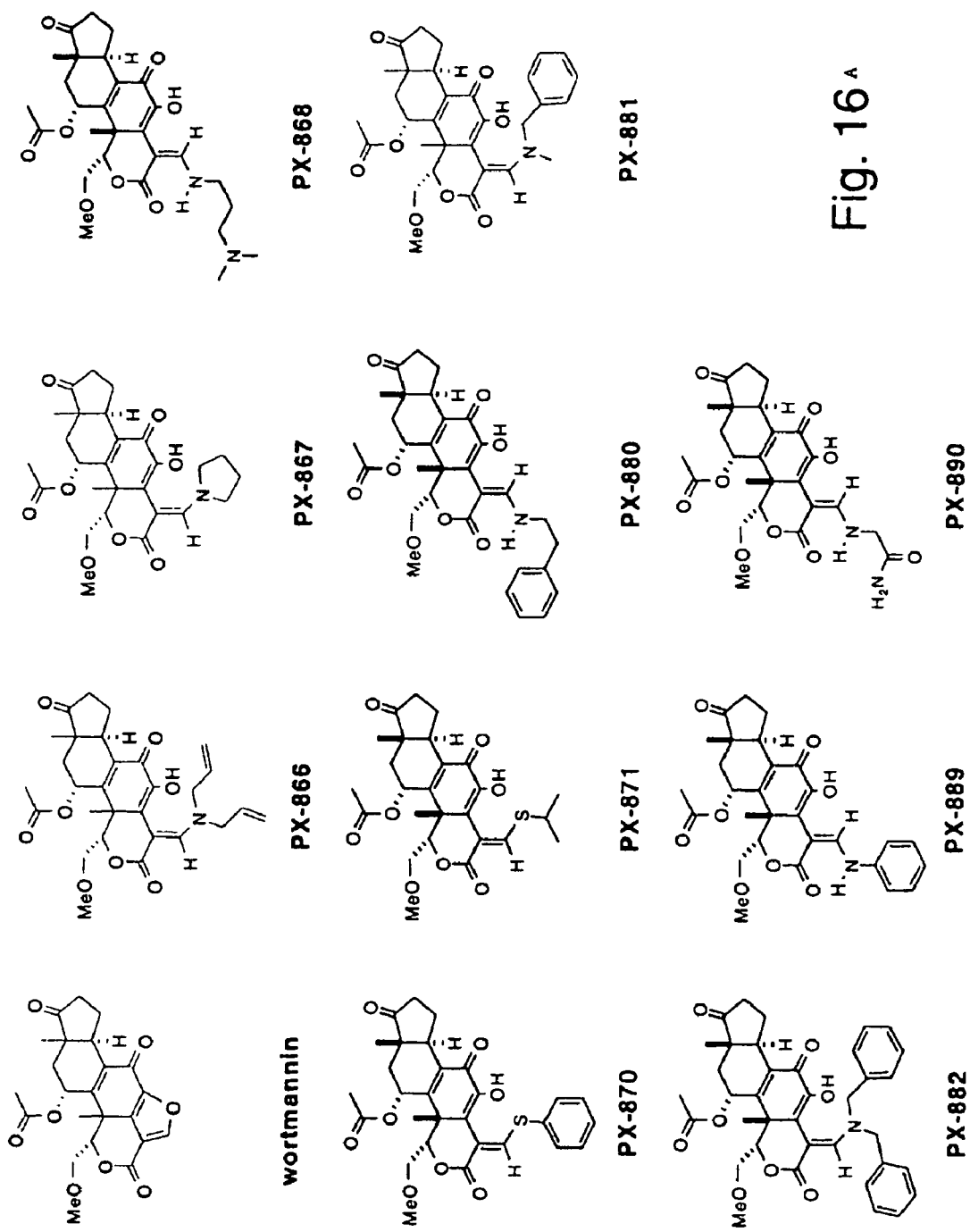
FIG. 16(A) and (B) are wortmannin analogs of the present invention.

One aspect of the present invention is wortmannin analogs of the following general formula:

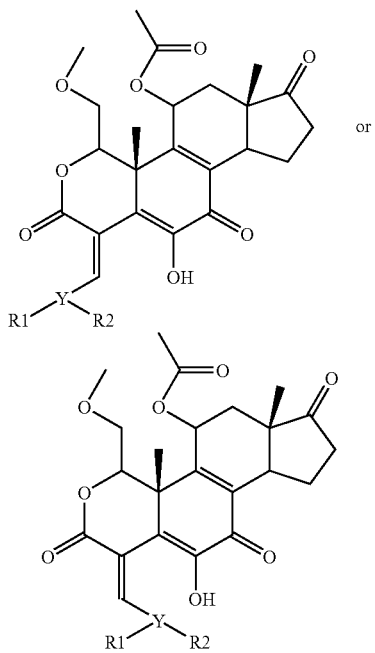

wherein Y is a heteroatom and R1 or R2 are unsaturated alkyl, non-linear alky, or substituted alkyl, including a branched alkyl or cyclic alkyl. Preferably, the wortmannin analog corresponds to the chemical formula selected from the group consisting of the compounds presented in FIG. 16. More preferably, R1 or R2 is a disubstituted alkyl, such as PX-866 and PX-867.

The biosynthetic production of wortmannin is well known in the art and the analogs are synthesized from wortmannin. U.S. Pat. No. 5,480,906, which is incorporated herein by reference in its entirety, describes typical synthetic schemes. Typically, wortmannin is produced by the fermentation of any one of a number of previously disclosed microorganisms such as Talaromyces wortmannin and Penicillium wortmannin, Myrothecium roridium, and Fusarium. Following fermentation, wortmannin is extracted and purified via known methods. Preferably, wortmannin is microbially synthesized and isolated in substantially pure form from a fermentation culture) one such fermentation culture is identified as A24603.1).

Culturing the strain under submerged aerobic conditions in a suitable culture medium until a recoverable amount of wortmannin is produced produces wortmannin. Wortmannin can be recovered using various isolation and purification procedures understood in the art.

The medium used to grow the culture can be any one of a number of media. For economy in production, optimal yield, and ease of product isolation, however, preferred carbon sources in large-scale fermentation are glucose and soluble starch such as corn starch. Maltose, ribose, xylose, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolyzed casein, beef extract, and the like can also be used.

Among the nutrient inorganic salts that can be incorporated in the culture media are the customary soluble salts capable of yielding calcium, magnesium, sodium, ammonium, chloride, carbonate, sulfate, nitrate, zinc, and like ions. Essential trace elements necessary for the growth and development of the organism also should be included in the culture medium. Such trace elements commonly occur as impurities in other substituents of the medium in amounts sufficient to meet the growth requirements on the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Following its production, wortmannin can be recovered from the fermentation medium by methods used in the art. The wortmannin produced during fermentation of the A24603.1 organism, for example, occurs mainly in the broth.

Typically, wortmannin can be recovered from the biomass by a variety of techniques. A preferred technique involves filtering whole fermentation broth with a ceramic filter. The filtrate is eluted with an organic solvent such as ethyl acetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

Wortmannin may be further manipulated to arrive at the compounds of the present invention. Although the synthesis of particular analogs of wortmannin are illustrated below, other synthetic schemes common in the art will allow one ordinarily skilled in the art to synthesize compounds in accordance with the present invention, and the synthetic schemes set forth herein should, in no way, be considered limiting.

For therapeutic treatment of the specified indications, a wortmannin analog of the present invention may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise a pharmaceutical carrier and at least one active compound selected from the group consisting of the term "active compound", as used throughout this specification, refers to at least one compound selected from compounds of the formulas or pharmaceutically acceptable salts thereof.

The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way.

In such a composition, the active compound is known as "active ingredient". In making the compositions, the active ingredient will usually be mixed with a carrier, or diluted by a carrier, or enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

By "pharmaceutically acceptable", it is meant the carrier, diluent or excipient must be compatible with the other ingredients of the formulation and not deleterious to the recipient thereof.

The local delivery of inhibitory amounts of active compound for the treatment of cancer can be by a variety of techniques that administer the compound at or near the proliferative site. Examples of local delivery techniques are not intended to be limiting but to be illustrative of the techniques available. Examples include local delivery catheters, site specific carriers, implants, direct injection, or direct applications. Local delivery by a catheter allows the administration of a pharmaceutical agent directly to the proliferative site.

Local delivery by an implant describes the surgical placement of a matrix that contains the pharmaceutical agent into the proliferative lesion. The implanted matrix releases the pharmaceutical agent by diffusion, chemical reaction, or solvent activators.

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989).

A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, Science 249: 1527-1533 (September, 1990) and Mathiowitz, et al., J. App. Poly. Sci., 26:809 (1981).

Local delivery by site specific carriers describes attaching the pharmaceutical agent to a carrier which will direct the drug to the proliferative lesion. Examples of this delivery technique include the use of carriers such as a protein ligand or a monoclonal antibody.

Local delivery by direct application includes the use of topical applications. An example of a local delivery by direct application is applying the pharmaceutical agent to the arterial tumor or area left behind after resection of the tumor.

Formulation of wortmannin analogs is well known in the art as is the fermentation process. Rather than get into exhaustive detail regarding synthetic scheme or formulation, the present invention relies on the skilled artisan to use those common synthetic and formulation techniques to synthesize compounds of the following general formula:

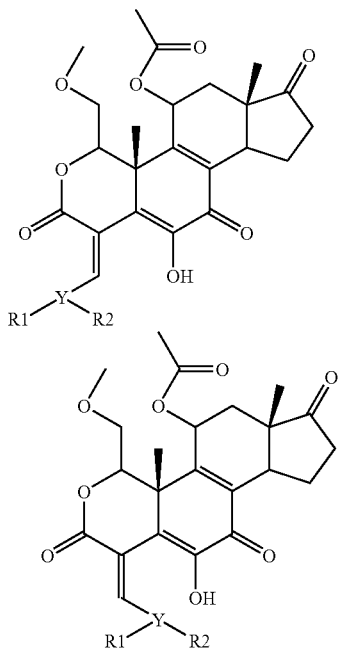

wherein Y is a heteroatom and R1 or R2 are unsaturated alkyl, non-linear alky, branched alky, substituted alkyl or cyclic alkyl. Preferably, the present invention has a chemical formula corresponding to a compound selected from the group consisting of the compounds presented in FIG. 16.

The wortmannin analogs and pharmaceutical compositions containing the same may be useful in the inhibition of PI-3K and useful in the treatment and/or prevention of cancer.

Another aspect of the present invention provides for the use of wortmannin analogs in combination with chemotherapeutic agents in the treatment and/or prevention of cancer. The wortmannin analogs may be administered prior to, during or following administration of a chemotherapeutic agent. Chemotherapeutic agents include both cytotoxic agents and anti-tumor targeting agents. Exemplary Cytotoxic agents include, but are not limited to, gemcitabine (Gemzar®), paclitaxel (Taxol®), and cisplatin (Platinol®). Exemplary anti-tumor targeting agents include, but are not limited to, gefitinib (Iressa®), erlotinib (Tarceva®), trastuzumab (Herceptin®), cetuximab (Erbitux®) and bevacizumab (Avastin®). In certain embodiments the pharmaceutical formulation may contain both a wortmannin analog and a chemotherapeutic agent in combination. In other embodiments, the wortmannin analog and the chemotherapeutic agent may be administered separately, either prior to, substantially simultaneously or after administration of the other agent.

In another aspect of the present invention, a method of inhibiting PI-3K by administering a therapeutically effective amount of a wortmannin analog of the following general formula:

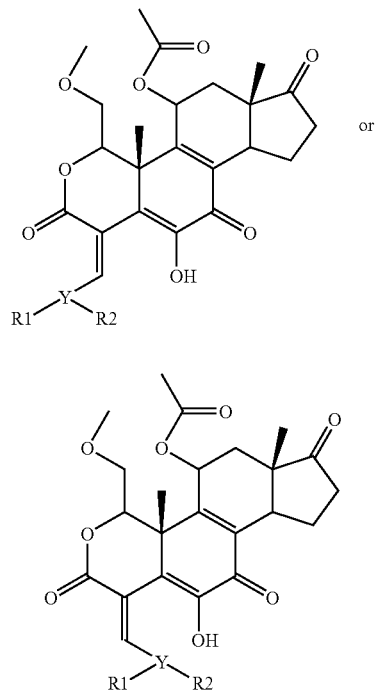

wherein Y is a heteroatom and R1 or R2 are unsaturated alkyl, non-linear alky, or substituted alkyl, including a branched alkyl or cyclic alkyl is provided. Preferably, the wortmannin analog corresponds to the chemical formula selected from the group consisting of the compounds presented in FIG. 16. More preferably, R1 or R2 is a disubstituted alkyl. In one embodiment the wortmannin analog is PX-866 and PX-867. The wortmannin analog may be administered prior to, substantially simultaneously with or after administration of the chemotherapeutic agent.

In another aspect of the present invention, a method of inhibiting PI-3K by administering a therapeutically effective amount of a wortmannin analog of the following general formula:

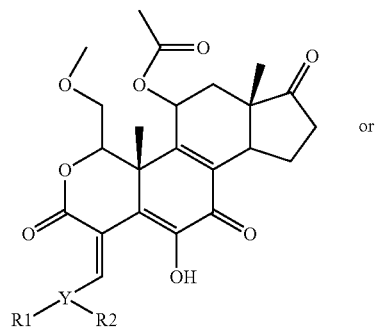

-continued

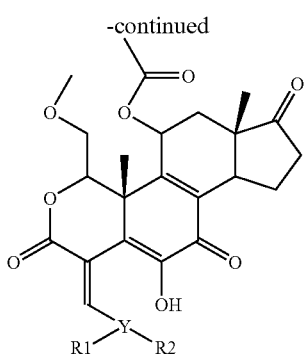

wherein Y is a heteroatom and R1 or R2 are unsaturated alkyl, non-linear alky, or substituted alkyl, including a branched alkyl or cyclic alkyl in combination with a chemotherapeutic agent is provided. Preferably, R1 or R2 of the wortmannin analog is a disubstituted alkyl and the chemotherapeutic agent is selected from the group consisting of gemcitabine (Gemzar®), paclitaxel (Taxol®), and cisplatin (Platinol®). Exemplary anti-tumor targeting agents include, but are not limited to, gefitinib (Iressa®), erlotinib (Tarceva®), trastuzumab (Herceptin®), cetuximab (Erbitux®) and bevacizumab (Avastin®). In a more preferred embodiment, the method comprises administering PX-866 and gefitinib. In another more preferred embodiment, the method comprises administering PX-867 and gefitinib. The wortmannin analog may be administered prior to, substantially simultaneously with or after administration of the chemotherapeutic agent.

In another aspect of the present invention, a method of treating or preventing cancer by administering a therapeutically effective amount of a wortmannin analog of the following general formula:

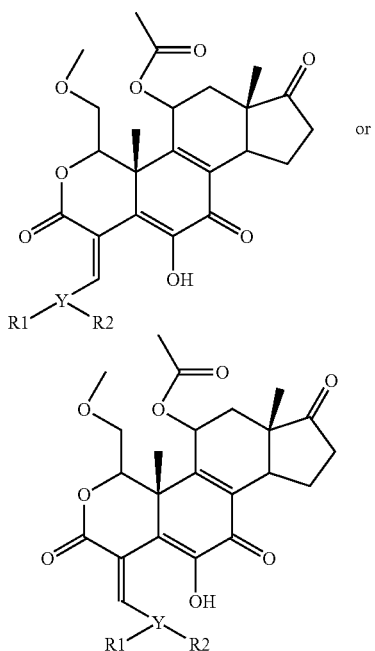

wherein Y is a heteroatom and R1 or R2 are unsaturated alkyl, non-linear alky, or substituted alkyl, including a branched alkyl or cyclic alkyl is provided. Preferably, the wortmannin analog corresponds to the chemical formula selected from the group consisting of the compounds presented in FIG. 16. More preferably, R1 or R2 is a disubstituted alkyl. In one embodiment the wortmannin analog is PX-866 and PX-867. The wortmannin analog may be administered prior to, substantially simultaneously with or after administration of the chemotherapeutic agent.

In another aspect of the present invention, a method of treating or preventing cancer by administering a therapeutically effective amount of a wortmannin analog of the following general formula:

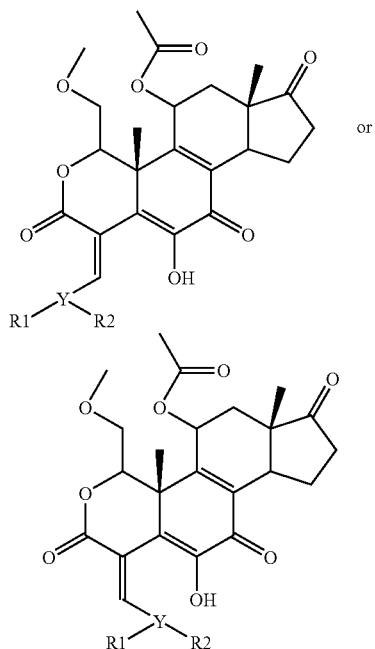

wherein Y is a heteroatom and R1 or R2 are unsaturated alkyl, non-linear alky, or substituted alkyl, including a branched alkyl or cyclic alkyl in combination with a chemotherapeutic agent is provided. Preferably, R1 or R2 of the wortmannin analog is a disubstituted alkyl and the chemotherapeutic agent is selected from the group consisting of gemcitabine (Gemzar®), paclitaxel (Taxol®), and cisplatin (Platinol®). Exemplary anti-tumor targeting agents include, but are not limited to, gefitinib (Iressa®), erlotinib (Tarceva®), trastuzumab (Herceptin®), cetuximab (Erbitux®) and bevacizumab (Avastin®). In a more preferred embodiment, the method comprises administering PX-866 and gefitinib. In another more preferred embodiment, the method comprises administering PX-867 and gefitinib. The wortmannin analog may be administered prior to, substantially simultaneously with or after administration of the chemotherapeutic agent.

In a further embodiment a compound comprising an active metabolite of a wortmannin analog and methods of using the same is provided. In a preferred embodiment, the active metabolite is selected from the group consisting of the carbonyl reduced and the carbonyl reduced deacetylated form of wortmannin analogs. In a preferred embodiment, the active metabolite is selected from the group consisting of carbonyl reduced PX-866 and carbonyl reduced deacetylated PX-866.

Increased cell survival is a fundamental characteristic of cancer cells and limits the effectiveness of cancer therapy. An important mechanism for increased cell survival in many cancers is mediated by the phosphatidylinositol-3-kinase (PtdIns-3-kinase)/Akt (protein kinase B) signaling pathway that is activated by receptor and oncogenic protein tyrosine kinases. Eight mammalian PtdIns-3-kinases are divided into 3 main classes; Class I PtdIns-3-kinasesphosphorylate membrane PtdIns to give PtdIns(3,4,5)P$_3$ which recruits the cytoplasmicserine/threonine kinase Akt by binding to its pleckstrin homology (PH) domain. Membrane associated Akt is activated by Ser$_{473}$ phosphorylation by membrane-associated phosphoinositidedependent kinase-1 (PDK1) and Thr$_{308}$ phosphorylation by a second incompletely characterized PDK2. Activated Akt detaches from the plasma membrane and moves to the cytoplasm and the nucleus, where it phosphorylates a battery of targets to prevent the expression of death genes, and induces cell survival. PtdIns-3-kinase activity is increased in human small cell lung cancer, ovarian, head and neck, urinary tract, colon and cervical cancers. The tumor suppressor protein PTEN (phosphatase and tensin homologue deleted onchromosome ten), a dual specificity tyrosine-threonine/PtdIns-3 phosphatase, prevents the accumulation of PtdIns(3,4,5)P$_3$ and attenuates PtdIns-3-kinase signaling (9). PTEN is mutated or deleted in a variety of human cancers including advanced prostate, endometrial, renal, glial, melanoma, and small cell lung cancers. PX-866 potentiates gefitinib antitumor activity. The protein kinase family has more that 800 human members among which receptor protein tyrosine kinases are frequently targets for cancer therapy. They include the epidermal growth factor receptor (EGFR, ErbB-1, HER1), that when activated by ligand binding to its extracellular domain, homo or heterodimerizes with any of 3 other family members, ErbB-2 (HER2), ErbB-3 (HER3) and ErbB-4 (HER4), leading to autophosphorylation of cytoplasmic Cterminaltyrosine residues. These phosphorylations recruit signal transducers leading to activation of signaling pathways that include the Ras-MEK-MAPK pathway, the STAT path way and the PtdIns-3-kinase/Akt survival pathway. The EGFR is amplified or over expressed in a wide range of human cancers where it is thought to play an important role in tumor progression. In non small cell (nsc) lung cancer EGFR expression is correlated with decreased patient survival. A number of small molecule inhibitors of the EGFR kinase as well as EGFR monoclonal antibodies are under development or approved for clinical use. Gefitinib (ZD 1839, Iressa®) is a small molecule EGFR inhibitor that when administered to patients with relapsed nsc lung cancer has shown a response rate of 10 to 20% and stabilized the disease in another 20 to 30% of patients. However, the addition of gefitinib to chemotherapy in untreated patients with nsc lung cancer had no effect on overall survival, time to progression, or response rate. A majority, but not all, nsc lung cancer patients responding to single agent gefitinib contain somatic mutations of unknown functional significance in the EGFR tyrosine kinase domain. However, there are also nsc lung cancer patients that do not have mutated EGFR receptors who may derive benefit from gefitinib and other EGFR inhibitors. Furthermore, even though activating mutations of the EGFR are rare in human colorectal cancer and glioblastoma some of these tumors may be responsive to EGFR inhibitors. A recent study has shown PX-866 potentiates gefitinib antitumor activity that gefitinib inhibits cell growth and down regulates PtdIns-3-kinase signaling only in nsc lung cancer cell lines with ErbB-3 expression. This is because PtdIns-3-kinase couples to ErbB-3 leading to PtdIns-3-kinase/Akt signaling activation only in nsc lung cancer cell lines with either wild type or mutant EGFR receptor, and ErbB-3. Gefitinib is able to block the association of PtdIns-3-kinase with ErbB-3, thus, preventing PtdIns-3-kinase/Akt activation in these cell lines.

The central role PtdIns-3-kinase plays in determining the response to gefitinib suggests that an inhibitor of PtdIns-3-kinase may provide a strategy to increase the antitumor activity of gefitinib in resistant nsc lung cancer tumors that do not express ErbB-3. PX-866 is a novel inhibitor of PtdIns-3-kinase that is currently in advanced preclinical development as an antitumor agent. The A-549 human nsc lung cancer cell line with mutant active Nras that does not express ErbB-3 and is resistant to gefitinib was used. It was found that in A-549 tumor xenografts gefitinib did not inhibit PtdIns-3-kinase/Akt signaling and the administration of PX-866 either intravenously (iv) or orally (po) markedly potentiated the antitumor activity of gefitinib. The toxicity of long term administration of PX-866 shows that it increases blood glucose associated with a decrease in insulin sensitivity.

This invention and embodiments illustrating the method and materials used may be further understood by reference to the following non-limiting examples.

EXAMPLE 1

Acetic acid 4-diallylaminomethylene-6-hydroxy-1-α-methoxymeth-yl-10β,13β-dimethyl-3,7,17-trioxo-1,3,4,7,10,11β,12,13,14α,15,16,17-dodecahydro-2-oxa-cyclopenta[α]phenanthren-11-yl ester (djm2-166).

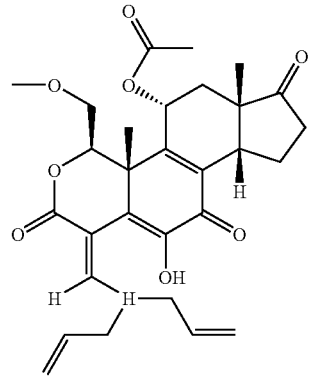

To a solution of wortmannin (10.7 mg, 25.0 μmol) in CH$_2$Cl$_2$ (125 μL) was added a freshly prepared 0.2 M stock solution of diallylamine (138 μL, 27.5 μmol) in CH$_2$Cl$_2$. The reaction mixture was stirred at room temperature for 1 h. The solvent and excess amine were removed in vacuo, and the product was purified via chromatography on SiO$_2$ (hexanes/ethyl acetate, 1:9) to give djm2-166 (9.0 mg, 17 μmol, 68%) as an orange oil: [α]$_D$=630 (c 0.0015, CH$_2$Cl$_2$,23 C); IR (KBr) 3391, 1743, 1695, 1685, 1622, 1569, 1222, 1111, 1100 cm$^{-1}$; $^1H$ NMR δ 8.20 (s, 1 H), 6.81 (s, 1 H), 6.06 (dd, 1H, J=7.4, 4.8 Hz), 5.85 (br s, 1 H), 5.62 (br, 1 H), 5.44-5.04 (m, 4 H), 4.48 (dd, 1H, J=7.2, 1.9 Hz), 4.05-3.60 (m, 4 H), 3.26 (s, 3 H), 3.27-3.20 (m, 1H), 3.16 (dd, 1H, J=10.9, 7.2 Hz), 3.00-2.90 (m, 2 H), 2.59 (dd, 1H, J=19.4, 8.6 Hz), 2.40 (dd, 1H, J=14.4, 7.7 Hz), 2.35-2.07 (m, 2 H), 2.07 (s, 3 H), 1.83 (dd, 1H, J=14.4, 4.7 Hz), 1.54 (s, 3H), 0.86 (s, 3 H); 13C NMR δ 217.0, 178.5, 169.6, 164.8, 156.3, 151.5, 139.0, 136.9, 132.2, 131.3, 127.7 (2 C), 119.2, 89.0, 81.9, 73.1, 67.6, 59.1, 50.9 (2 C), 48.9, 42.3, 42.2, 37.5, 36.0, 24.6, 22.2, 20.8, 16.1; MS (EI) m/z (rel. intensity) 525 (M$^+$, 11), 466 (17), 391 (15), 350 (14), 323 (13), 266 (17), 239 (17), 60 (100); HRMS (EI) calculated for C$_{29}$H$_{35}$NO$_8$ 525.2363, found 525.2386.

EXAMPLE 2

Acetic acid 6-hydroxy-1α-methoxymethyl-10β,13β-dimethyl-3,7,17-trioxo-4-pyrrolidin-1-yl-methylene-1,3,4,7,10,11β,12,13,14α,15,16,17-dodecahydro-2-oxa-cyclopenta[α]phenanthren-11-yl (djm2-167).

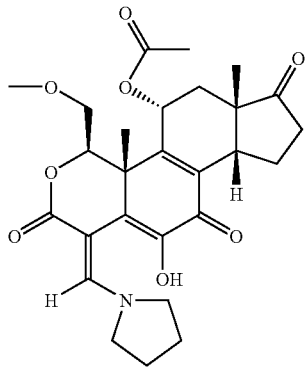

To a solution of wortmannin (30.0 mg, 70.0 μmol) in CH$_2$Cl$_2$ (200 μL) was added pyrrolidine (7.0 μL, 84 μmol) in CH$_2$Cl$_2$. The reaction mixture was stirred at room temperature for 1 h. The solvent and excess thiol were removed in vacuo and the product was purified by chromatography on SiO$_2$ (hexanes/ethyl acetate 9:1, then 1:1) to give djm2-167 (30.0 mg, 60.6 μmol, 86%) as an orange oil: [α]$_D$ −390 (c 0.0073, CH$_2$Cl$_2$, 23 C); IR (KBr) 3337, 1740, 1684, 1617, 1570, 1261, 1221, 1099, 1018 cm.sup.-1; .sup.1H NMR δ 8.29 (s, 1 H), 6.72 (s, 1 H), 6.07 (dd, 1H, J=6.9, 4.8 Hz), 4.47 (dd, 1H, J=7.0, 1.9 Hz), 3.80-3.70 (m, 2 H), 3.25 (s, 3 H), 3.25-3.14 (m, 2 H), 3.02-2.90 (m, 2 H), 2.69 (br s, 1 H), 2.58 (dd, 1H, J=19.1, 8.4 Hz), 2.39 (dd, 1H, J=14.6, 7.8 Hz), 2.32-2.08 (m, 2 H), 2.06 (s, 3 H), 1.99-1.95 (m, 5 H), 1.84 (dd, 1H, J=14.5, 4.2 Hz), 1.56 (s, 3 H), 0.86 (s, 3 H); .sup.13C NMR δ 217.5, 178.9, 169.9, 164.9, 153.9, 151.3, 137.6, 137.1, 129.2, 89.4, 82.1, 73.3, 67.7, 59.3, 55.2, 49.2 (2 C), 42.6, 42.4, 37.8, 36.3, 25.6 (2 C), 24.5, 22.4, 21.0, 16.3; MS (EI) m/z (rel. intensity) 499 (M.sup.+, 1), 439 (2), 365 (7), 167 (35), 149 (100); HRMS (EI) calculated for C$_{27}$H$_{33}$NO$_8$ 499.2206, found 499.2191.

EXAMPLE 3

Acetic acid 4-[(benzylmethylamino)methylene]-6-hydroxy-1α-methoxymethyl-10β,13β-dimethyl-3,7,17-trioxo-1,3,4,7,10,11β,12,13,14α,15,16,17-dodecahydro-2-oxa-cyclo penta[α]phenanthren-11-yl ester (djm2-181).

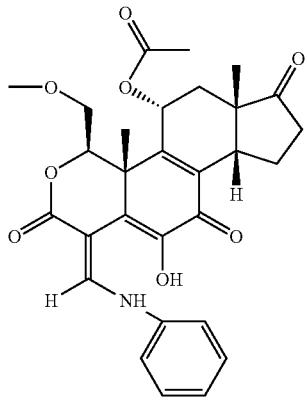

To a solution of wortmannin (10.7 mg, 25.0 μmol) in of CH$_2$Cl$_2$ (125 μL) was added a freshly prepared 0.2 M solution of N-methylbenzylamine (185 μL, 37.0 μmol) in CH$_2$Cl$_2$. The reaction mixture was stirred at room temperature for 2 h. The solvent was removed in vacuo, and the product was purified by chromatography on SiO$_2$ (hexanes/ethyl acetate, 1:9) to give djm2-181 (13.3 mg, 24.2 μmol, 97%) as an orange oil: [α]$_D$ −835 (c 0.0014, CH$_2$Cl$_2$, 23 C); IR (neat) 1742, 1685, 1618, 1589, 1575, 1224 cm$^{-1}$; $^1$H NMR δ 8.36 (br s, 1 H), 7.36-7.27 (m, 5 H), 6.60 (bs s, 1 H), 6.10-6.00 (m, 1 H), 4.68-4.63 (m, 1 H), 4.53-4.47 (m, 2 H), 3.25 (s, 3 H), 3.25-3.11 (m, 2 H), 2.99-2.84 (m, 2 H), 2.71 (br, 2 H), 2.55 (dd, 1H, J=19.5, 8.9 Hz), 2.38 (dd, 1H, J=14.4, 7.6 Hz), 2.32-2.05 (m, 2 H), 2.05 (s, 3 H), 1.85 (br s, 1 H), 1.80 (dd, 1H, J=14.5, 4.7 Hz), 1.52 (s, 3 H), 0.82 (s, 3 H); $^{13}$C NMR δ 217.3, 178.9, 169.9, 164.7, 158.3, 151.7, 138.8, 137.1, 134.9, 129.0 (3 C), 128.6, 128.1 (2 C), 88.7, 82.2, 73.4, 67.9, 64.3, 59.4, 49.1, 42.7, 42.5, 37.8 (2 C), 36.3, 25.2, 22.5, 21.1, 16.3; MS (EI) m/z (rel. intensity) 549 (M+, 14), 489 (37), 415 (15), 120 (23), 91 (100); HRMS (EI) calculated for C$_{31}$H$_{35}$NO$_8$ 549.2363, found 549.2340.

EXAMPLE 4

The pharmacodynamics of various wortmannin analogs were tested. In particular, the effect of dose of PX-866, PX-867 and PX-881 was measured on inhibition of HT-29 xenograft phosphor-Akt. FIG. 1A illustrates that inhibition was increased as the dose of the wortmannin analog was increased. PX-866 appeared to exhibit the greatest inhibitory activity. The effect of the route of administration on the inhibitory activity of PX-866 over time was also measured. PX-866 was administered intraperitoneal, intravenously and orally. As shown in FIG. 1B, notably, the oral formulation of PX-866 appeared to provide more consistent inhibition over a longer period of time.

The pharmacokinetics of intravenous, intraperitoneal and oral administration of PX-866 in vivo was measured and is depicted in FIG. 2. Based on the foregoing it appears that the half-life of PX-866 is about 16 hours.

The metabolism of PX-866 following oral administration was observed. Generally, PX-866 is metabolized into a carbonyl reduced and carbonyl reduced deacetylated metabolites, as depicted below.

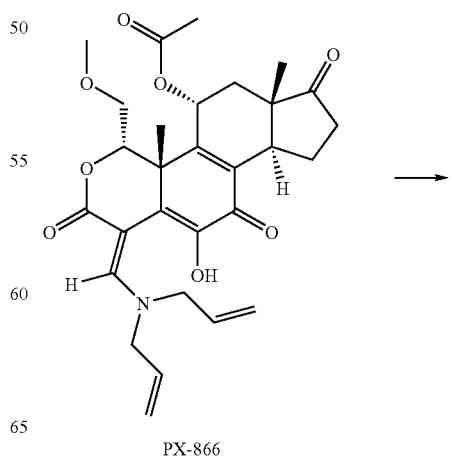

PX-866

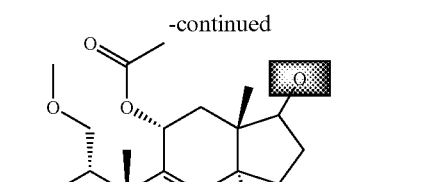

Figure 3:
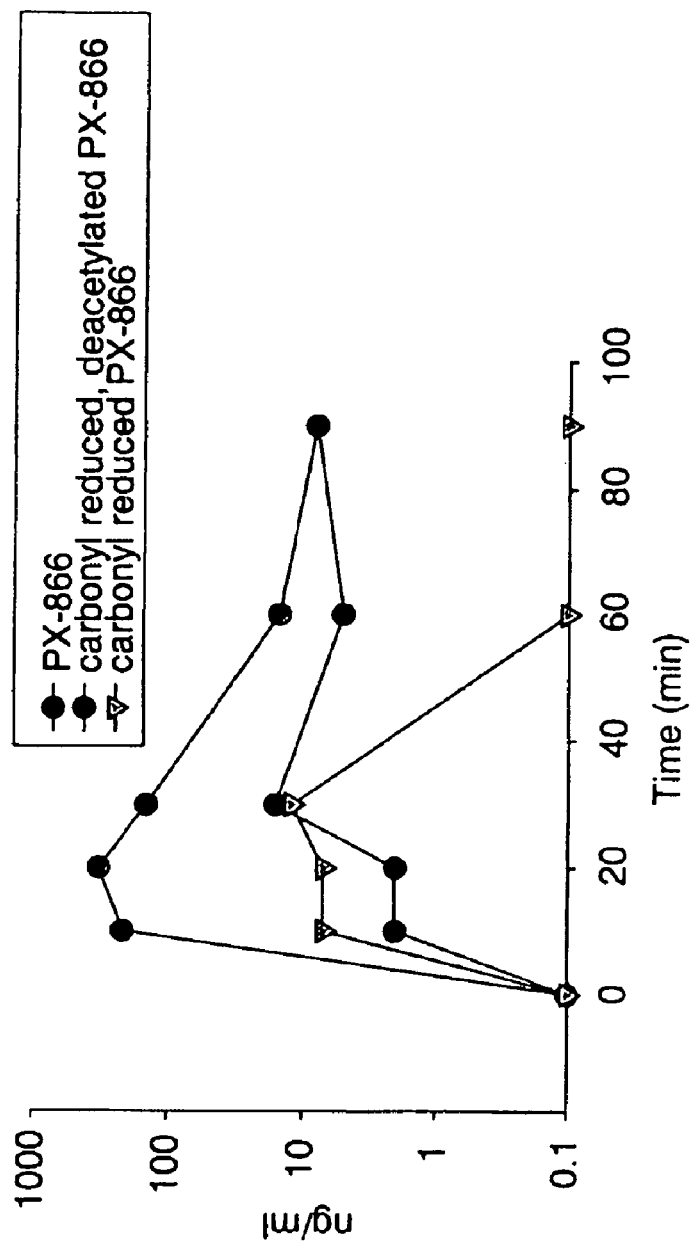
FIG. 3 is a graph of the concentration of PX-866 and metabolites (in ng/ml) in mouse plasma.

As shown in FIG. 3, the most abundant component is PX-866, followed by the carbonyl reduced metabolite, and then the carbonyl reduced, deacetylated metabolite, however following about 40 minutes at administration it appears that the carbonyl reduced PX-866 is further metabolized to the carbonyl reduced, deacetylated metabolite. Based upon the foregoing, the T½ of the major metabolite is about at least 3 hours.

EXAMPLE 5

Figure 4A:
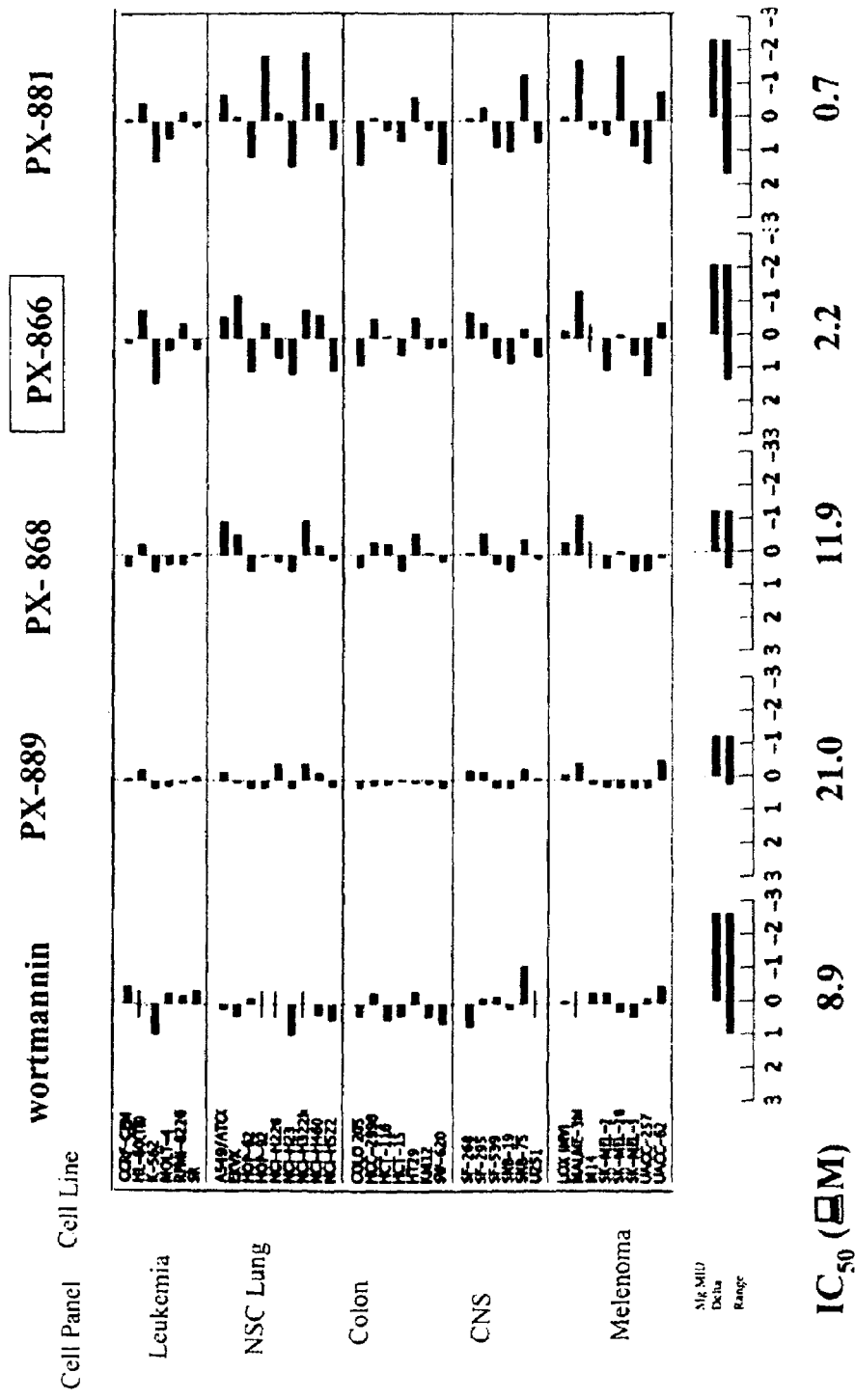
FIG. 4 depicts the activity of wortmannin analogs of the present invention in the NCI human tumor cell line panel, as measured by $IC_{50}$.
Figure 4B:
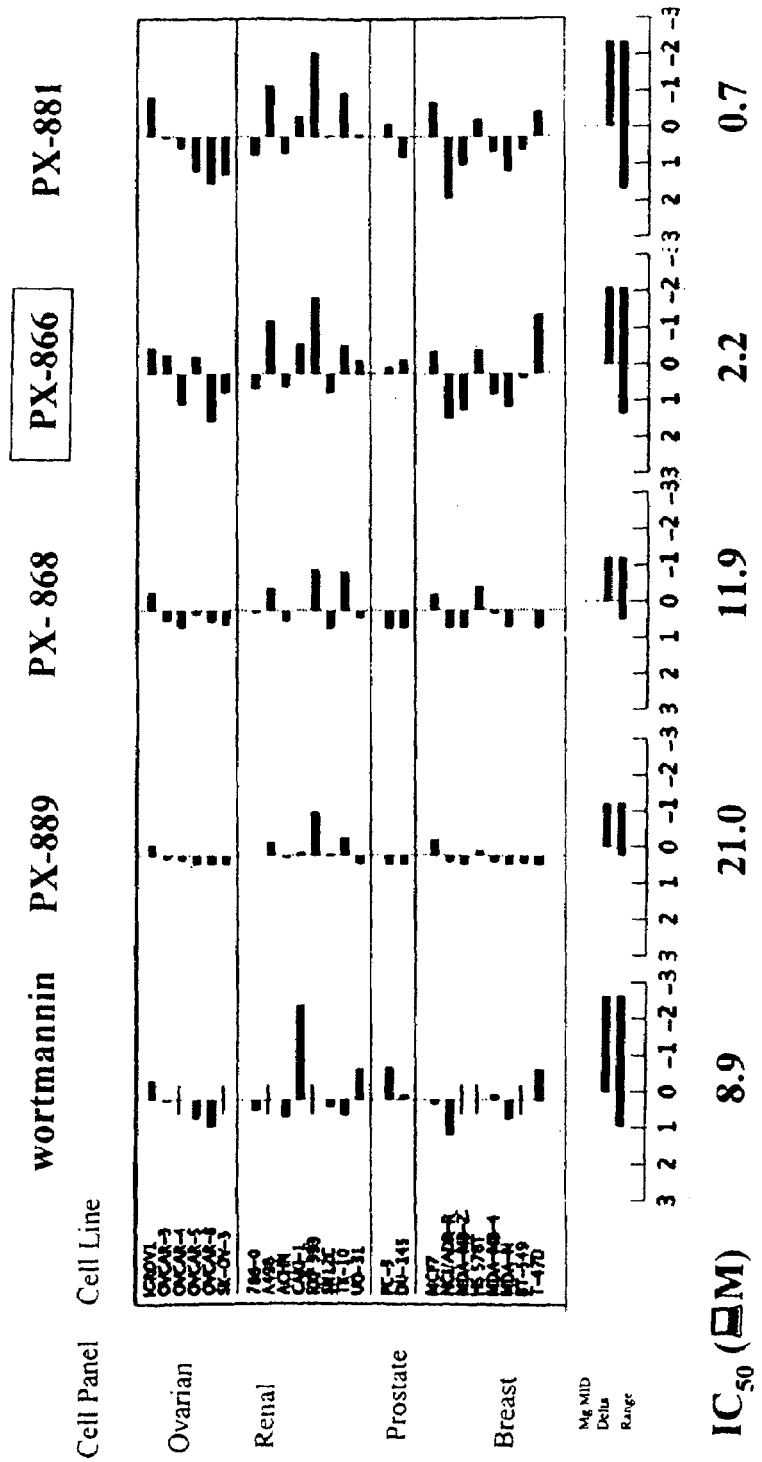

The activity of wortmannin analogs in the NCI human tumor cell line panel was measured. Specifically, the activity of wortmannin, PX-889, PX-868, PX-866 and PX-881 was measured in leukemia, NSC lung, colon, CNS, melanoma, ovarian, renal, prostate and breast cancer cell lines as measured by IC50. Results are depicted in FIG. 4.

EXAMPLE 6

Figure 5:
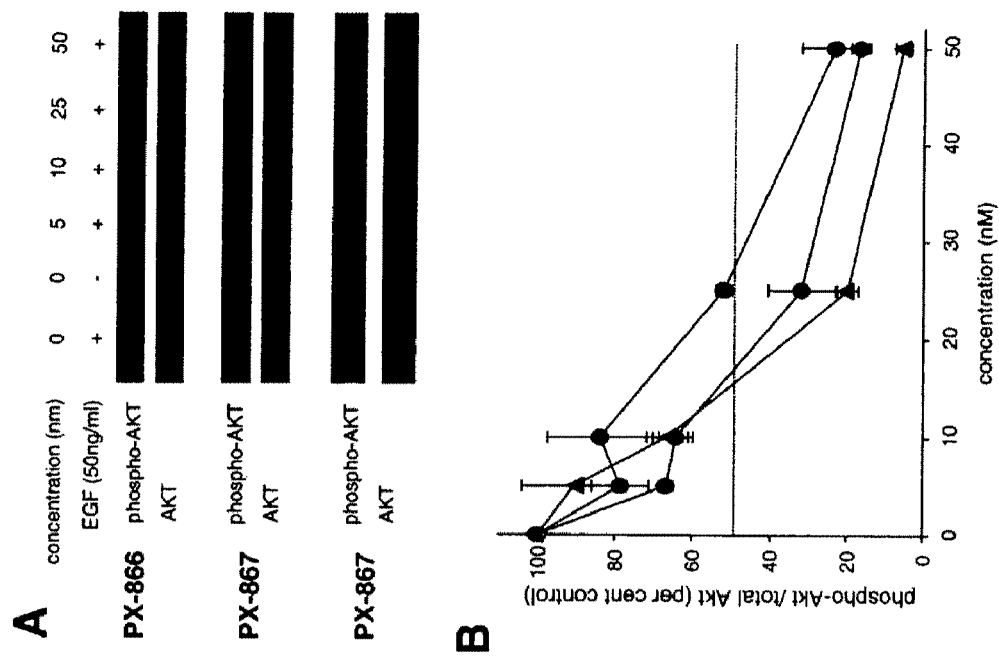
FIG. 5A and 5B are, respectively a Western blot depiciting total protein amounts of phospho-Akt and Akt in HT-29 colon cancer cells following administrasions of wortmannin analogs of the present invention and a graph showing the percent inhibition of HT-29 colon cancer cell phospho-Akt by wortmannin analogs of the present invention.

The inhibition of HT-29 colon cancer call phospho-Akt, as measured by percent control, was measured by administration of PX-866 and PX-867. Results are depicted in FIG. 5.

EXAMPLE 7

The antitumor activity of wortmannin analogs was measured. As shown in Table 1, below, the analogs exhibited antitumor activity against ovarian, colon and lung derived tumors in vivo.

TABLE 1

| Tumor | Initial tumor vol (mm³) | Compound | mg/kg/day | Route | Schedule | T/C[a] % (day) | Growth Delay (day) | $Log_{10}$ cell kill | p |
|---|---|---|---|---|---|---|---|---|---|
| OvCaR-3 ovarian | 120 | wortmannin | 0.75 | ip | Q1D × 9 | 47 (40) | 5 | 0.5 | * |
| | 120 | PX-866 | 8 | ip | Q1D × 9 | 30 (40) | 12 | 1.2 | * |
| | 120 | PX-867 | 13 | ip | Q1D × 9 | 41 (40) | 6 | 0.6 | * |
| | 120 | PX-881 | 12 | ip | Q1D × 9 | 52 (40) | 8 | 0.8 | * |
| HT-29 colon | 180 | wortmannin | 0.75 | ip | Q1D × 9 | 36 (16) | 5 | 0.3 | * |
| | 170 | PX-866 | 12 | ip | Q1D × 9 | 39 (16) | 6 | 0.4 | * |
| | 170 | PX-867 | 13 | ip | Q1D × 9 | 80 (16) | 0 | 0 | |
| | 170 | PX-881 | 12 | ip | Q1D × 9 | 62 (16) | 2 | 0.2 | |
| A-549 lung | 65 | PX-866 | 6 | ip | Q1D × 9 | 62 (32) | 4 | 0.2 | |
| | 65 | PX-866 | 9 | ip | Q1D × 9 | 26 (32) | 8 | 0.4 | * |
| | 60 | PX-866 | 12 | iv | Q1D × 9 | 45 (21) | 5 | 0.7 | * |
| | 60 | PX-866 | 4 | po | Q1D × 9 | 47 (21) | 6 | 0.9 | * |

[a]T/C = optimal test/control as % and the day in parenthesis; p < 0.05 compared to non drug treated control tumor growth rate

EXAMPLE 8

Figure 6:
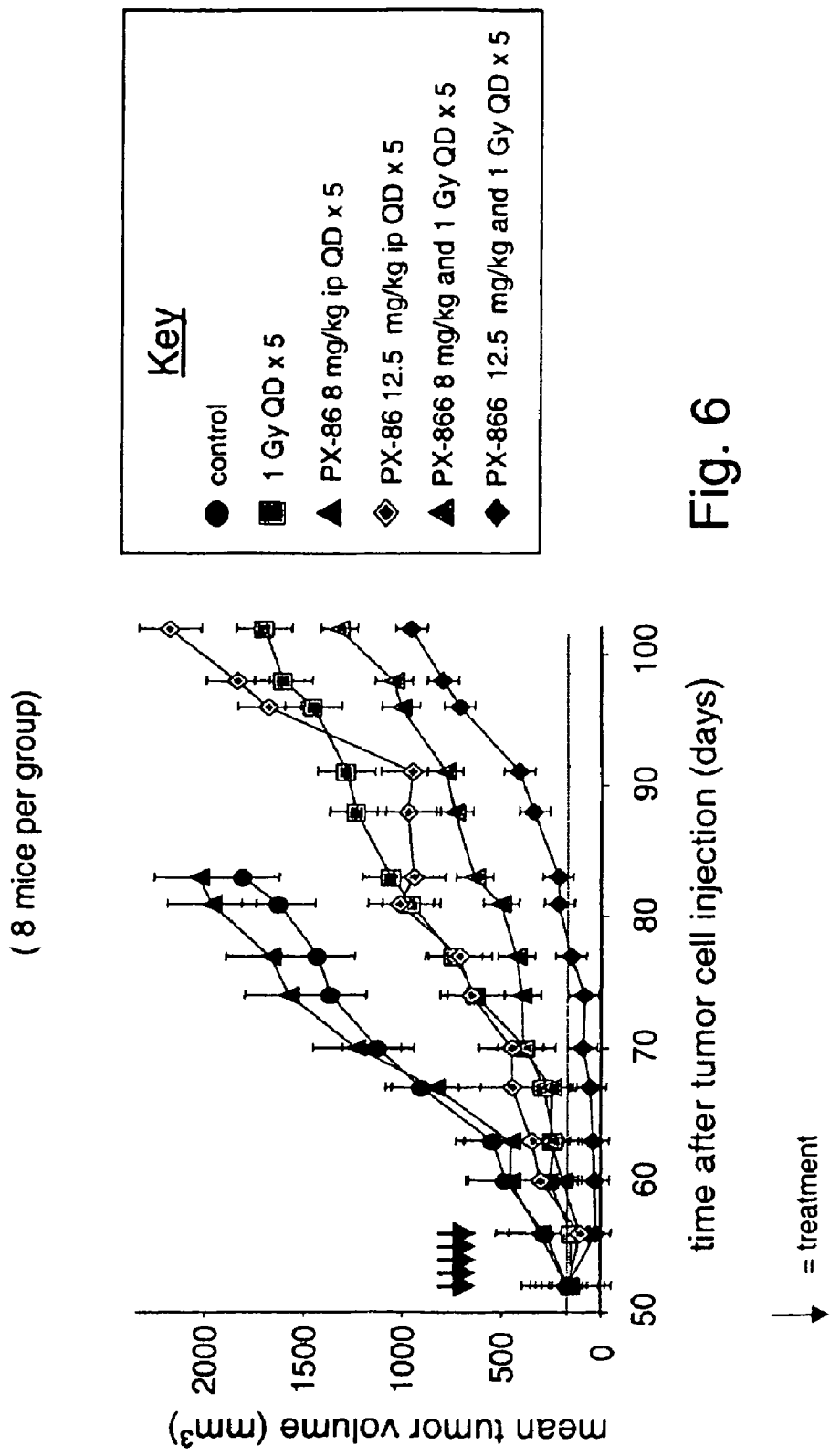
FIG. 6 is a graph of the mean tumor volume (in $mm^3$) following treatment with PX-866, a wortmannin analog of the present invention, alone or in combination with radiation in OvCar-3 human ovarian xenografts.

The antitumor activity of radiation alone, PX-866 alone or in combination with radiation was measured in OvCar-3 human ovarian xenografts in mice, as show in FIG. 6. Radiation was administered daily for 5 days and compared to administration of PX-866 at 8 and 12.5 mg/kg IP daily for 5 days or in combination with radiation. Results were measured in terms of mean tumor volume.

EXAMPLE 9

The antitumor activity of various cytotoxic drugs alone or in combination with PX-866 was measured. Cytotoxic agents included gemcitabine, taxol and cisplatin. As shown in Table 2, below, PX-866 significantly increased the percent to tumor growth inhibition and delay in growth over treatment with the cytotoxic agents alone in pancreatic, ovarian, lung and colon cancer cell lines.

lines were tested to be mycoplasma free using a PCR ELISA kit (Roche Diagnostics Inc., Indianapolis, Ind.).

Measurement of PtdIns-3-kinase. The ability of PX-866 to inhibit recombinant bovine p110α/p85α and recombinant human p110β/p85α, p120 (and p110*/p85α was measured by the [32 P](-ATP dependent phosphorylation of PtdIns as described by Stirdivant et al (22). Inhibition of cellular PtdIns-3-kinase was measured as the ratio of phosphoSer473-Akt to total Akt measured by Western blotting, as previously described.

Antitumor Studies. Approximately 107 A-549 nsc lung cancer cells in log cell growth were injected subcutaneously in 0.2 ml phosphate buffered saline into the flanks of severe combined immunodeficient (scid) mice. When the tumors reached 100 or 600 mm3 the mice were stratified into groups of 8 animals having approximately equal mean tumor volumes and drug administration was started. Dosing was every other day with gefitinib at 75 mg/kg po; PX-866 at 4, 9 or 12

TABLE 2

| Tumor | Size mm$^3$ | Drug | Route | Dose mg/kg | Schedule | TGI % | Alone Growth delay days | log cell kill | Combined TGI % | Growth delay days | log cell kill |
|---|---|---|---|---|---|---|---|---|---|---|---|
| P--------- anc-1 pancreatic | 75 | gemcitabine | ip | 150 | Q3D × 3 | 38 | 7 | 0.2 | | | |
| | | PX-866 | iv | 15 | Q3D × 3 | 16 | 4 | 0.1 | 49 | 8 | 0.2 |
| | | PX-866 | po | 5 | Q3D × 3 | 14 | 0 | 0 | 60 | 19 | 0.5 |
| OvCar-3 ovarian | 110 | taxol | ip | 12 | Q2D × 5 | 58 | 13 | 1.0 | | | |
| | | PX-866 | iv | 12 | Q2D × 5 | 58 | 12 | 0.9 | 83 | 20 | 1.5 |
| | | PX-866 | po | 4 | Q2D × 5 | 53 | 11 | 0.82 | 87 | 34 | 2.6 |
| A-549 lung | 300 | cisplatin | ip | 1 | QD × 5 | 16 | 1 | 0.1 | | | |
| | | PX-866 | ip | 6 | QD × 5 | 27 | 3 | 0.30 | 58 | 10 | 1.0 |
| HT-29 colon | 150 | cisplatin | ip | 2.5 | Q2D × 3 | 11 | 0 | 0 | | | |
| | | PX-866 | iv | 10 | Q2D × 3 | 11 | 0 | 0.3 | 56 | 6 | 0.5 |
| | | PX-866 | po | 2.5 | Q2D × 3 | 29 | 1 | 0.1 | 63 | 8 | 0.7 |

TGI (tumor growth inhibition) = 100 − T/C %

EXAMPLE 10

Materials and Methods. Compounds. PX-866 (acetic acid (1S,4E,10R,11R,13S,14R)-[4-diallylaminomethylene-6-hydroxy-1-methoxymethyl-10,13-dimethyl-3,7,17-trioxo-1,3,4,7,10,11,12,13,14,15,16,17-dodecahydro-2-oxa-cyclopenta [α]phenanthren-11-yl ester) was synthesized as previously described (21). For IV administration to mice PX-866 was dissolved at 10 mg/ml in 5% ethanol in 0.9% NaCl, and for po administration at 5 mg/ml in 5% ethanol in water. Gefitinib was obtained from Astra Zeneca (Macclesfield, UK) and suspended at 7.5 mg/ml in 0.1% Tween 20 in water for po administration. Rabbit purified anti-phosphoSer473-Akt antibody, anti-Akt antibody, antiphospho Tyr1086-EGF-receptor antibody and anti-EGFR antibody were obtained from Cell Signaling Technology (Beverly, Mass.). Human recombinant p110α/p85α, p110β/p85α, p120 (and p110*/p85α PtdIns-3-kinases were obtained from Upstate (Charlottesville, Va.). Metformin hydrochloride was obtained from Spectrum Chemical (Gardena, Calif.), pioglitazone hydrochloride and recombinant human insulin from Sigma Chemical (St. Louis).

Cells. A-549 non small cell lung cancer cells were obtained from the American Tissue Type Collection (Rockville, Md.). The cells were grown in humidified 95% air, 5% CO2 at 37° C. in Dulbecco=s modified Eagle=s medium (DMEM) supplemented with 10% fetal bovine serum (fbs). All cell mg/kg iv; PX-866 at 1, 2.5 and 3 mg/kg po, or PX-866 administered 4 hr before gefitinib. Animals were weighed weekly and tumor diameters were measured twice weekly at right angles (d short and d long) with electronic calipers and tumor volumes calculated by the formula volume=(dshort)2× (dlong))2. When the tumor reached 2,000 mm3 or more, or became necrotic the animals were euthanized.

Pharmacodynamic Studies. 10$^7$ A-549 nsc lung cancer cells were injected subcutaneously into the flanks of male scid mice and allowed to grow to approximately 300 mm3. Mice were administered PX-866 12 mg/kg iv, 3 mg/kg po and gefitinib 75 g/kg po, every other day for 5 days. Tumors were removed 24 hr after the last dose and immediately frozen in liquid N2. For assay, the tumors were homogenized in 50 mM HEPES buffer, pH 7.5, 50 mM NaCl, 1% Nonidet P40 and 0.25% sodium deoxycholate and Western blotting performed using anti-phosphoSer473-Akt and anti Akt antibodies. Tumor Akt activity was expressed as the ratio of phosphoSer473-Akt to total Akt.

Toxicity Studies. Male scid mice were administered PX-866 at 10 mg/kg iv, or 3 and 1.5 mg/kg po, every other day for 14 doses. C57B1/6 mice were administered PX-866 at 3 mg/kg po every other day for 15 doses. The mice were killed 24 hr after the last dose and changes in body weight, blood lymphocyte, neutrophil, red blood cell, platelet counts, serum glucose, aspartate amino transferase (AST), and amino alanine transferase (ALT) were measured.

Glucose Tolerance Studies. Female C5781/6 mice were fasted overnight and administered a single dose of D(+) glucose (1 mg/kg) as a 0.1 g/ml solution po. Blood was collected at 0, 10, 20, 30, 60, 90, 120 and 180 min and plasma glucose measured using a blood glucose kit (Sigma Chemical Co., St Louis, Mo.) to obtain a plasma glucose area under the curve (AUC 0-180 min). Mice were administered PX-866 10 mg/kg po as a single dose and glucose administered 4 hours later, or 3 mg/kg PX-866 po every other day for 20 doses and glucose administered 24 hours and 8 days after the last dose. Metformin was administered at 250 mg/kg po daily for 5 days (24) and 10 mg/kg pioglitazone ip daily for 7 days (25) before the glucose administration. Human recombinant insulin was administered at 0.075:g/kg ip (26) at the same time as glucose administration.

Bone Marrow Colony Formation. After sacrifice, mouse bone marrow was extracted from each femur and red blood cells lysed with 0.2% hypotonic NaCl followed by the addition of a 1.6% hypertonic NaCl. Approximately 20,000 cells were plated in 1 ml of Methocult™ GF M3434 (Stemcell Technologies Inc, Vancouver, BC, Canada) containing 1% methylcellulose in Iscove's Minimum Essential Media, 15% fbs, 1% bovine serum albumin, 10:g/ml recombinant human insulin, 200:g/ml humantransferrin, 10 mM β-mercaptoethanol, 2 mM L-glutamine, 50 ng/ml rm stem cell factor, 10 ng/ml recombinant mouse interleukin-3, 10 ng/ml recombinant human interleukin-6, and 3 units/ml recombinant erythropoietin. Cells were plated in triplicate and grown at 37/C and 5% CO2 in a humid environment for 14 days before scoring. Colonies (>40 cells/colony) or clusters (3-40 cells) were scored and growth of colony-forming unit granulocyte, erythroid, macrophage, megakaryocyte (CFU-GEMM; burst-forming units-erythroid (BFU-E), colony-forming units granulocyte macrophage (CFU-GM), assessed using standard criteria. Qualitative observations were made on background levels of single cells.

Results. PtdIns-3-kinase inhibition. The ability of PX-866 to inhibit recombinant PtdIns-3-kinases compared to inhibition by wortmannin is shown in Table 3. PX-866 and wortmannin are potent inhibitors of p110α, p120 (and p110* but unlike wortmannin PX-866 is a poor inhibitor of p110β.

TABLE 3

Inhibition of PtdIns-3-kinases by PX-866 and wortmannin.

| PtdIns-3-kinase | PX-866 $IC_{50}$ (nm) | wortmannin $IC_{50}$ (nm) |
| --- | --- | --- |
| p110α/p85α | 5.5 | 4.0 |
| p110β/p85α | >300 | 0.7 |
| p120γ | 9.0 | 9.0 |
| p110δ/p85α | 2.7 | 4.1 |

Cell culture studies. PX-866 inhibited phospho-Akt in A-549 human breast cancer cells in media containing 10% fbs with an $IC_{50}$ of 25 nM. Gefitinib only inhibited phospho-Akt in cells that were serum starved for 24 hr and then stimulated with EGF 25 ng/ml but not in media with 10% fbs. This suggests that the PtdIns-3-kinase pathway is stimulated by growth factors in serum, in addition to EGF. Cell growth inhibition studies confirmed previous reports that A-549 cells are resistant to growth inhibition by gefitinib, with an $IC_{50}$ of 1.1:M. PX-866 at concentrations up to 100 nM did not enhance the growth inhibition by gefitinib.

Figure 7:
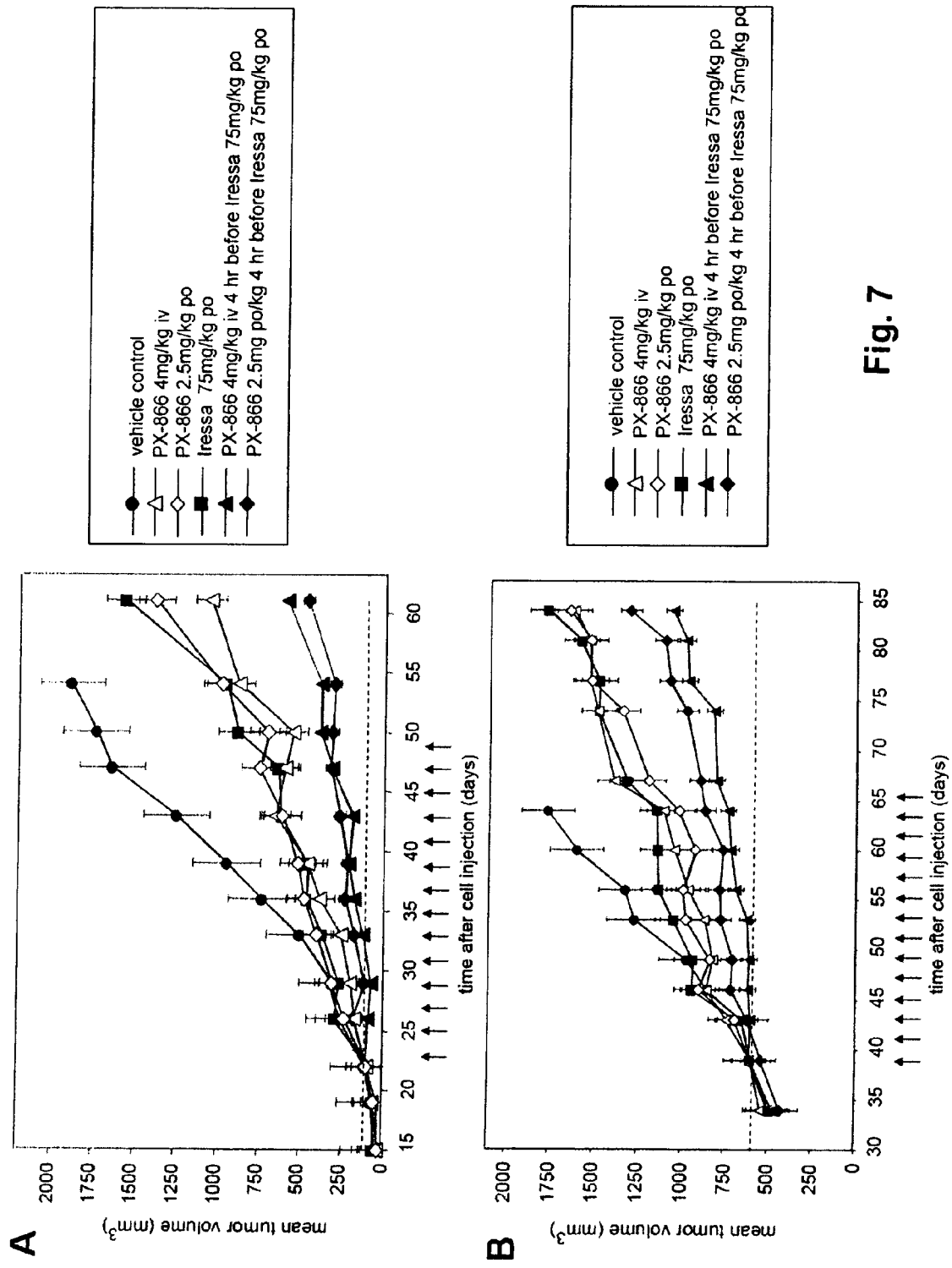
FIG. 7 is a graph illustrating the potentiation of the antitumor activity of gefitinib by PX-866 of initial tumor size of about (A) 100 $mm^3$ A-549 tumor xenograft and (B) 600 $mm^3$ A-549 timor xenograft.

In vivo antitumor studies. Administration of gefitinib at 75 mg/kg po every other day to mice with 100 mm3 A-549 human nsc lung cancer xenografts inhibited xenograft growth with a T/C of 51% at the end of the dosing period (FIG. 7). PX-866 is approximately 4 times more potent as an antitumor agent when given po than given iv, and doses were adjusted accordingly (Table 4). Female scid mice were implanted subcutaneously in the flank with 107 A-549 human nsc lung cancer cells. Tumors were allowed to grow to a mean volume of 100 mm before drug treatment was started every other day for 14 doses. Antitumor activity is expressed as the % volume of the treated tumor/control tumor (T/C %) at the end of the dosing period. There were 8 mice in each group and all differences are p<0.01.

TABLE 4

Antitumor Activity of PX-866 in combination with gefitinib

| Treatment and Route | Dose mg/kg | Schedule | Tumor T/C % | PX-844 4 hrs before gefitinib Tumor T/C % |
| --- | --- | --- | --- | --- |
| gefitinib po | 75 | QOD × 14 | 50.8 | — |
| PX-866 IV | 4 | QOD × 14 | 65.3 | 20.5 |
| PX-866 IV | 9 | QOD × 14 | 31.5 | 22.3 |
| PX-866 PO | 1 | QOD × 14 | 54.8 | 40.8 |
| PX-866 PO | 2.5 | QOD × 14 | 40.8 | 18.1 |

When administered alone to mice with 100 mm3 A-549 tumor xenografts, PX-866 inhibited tumor growth with T/Cs of 31% at 9 mg/kg iv and 41% at 2.5 mg/kg po. Preliminary studies showed that PX-866 in combination with gefitinib on an alternating day schedule was more active when administered 4 hr before rather than 24 hr after gefitinib (data not shown). When PX-866 was administered 4 hr before gefitinib the combination gave T/Cs of 22% at 9 mg/kg PX-866 iv and 18% at 2.5 mg/kg PX-866 po. Tumor growth was held stationary for the first half of the treatment period with PX-866 and then began to slowly increase towards the end of the period (FIG. 7). Increased combination antitumor activity was also seen with very large 600 mm3 A-549 tumor xenografts (FIG. 7B).

Figure 8:
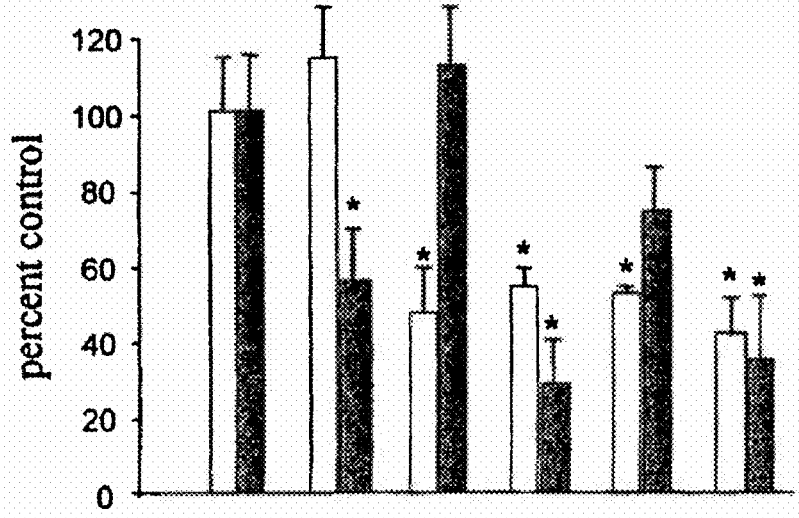
FIG. 8A and 8B are, respectively, a Western blot depicting total protein amounts of p-AKT $Ser^{473}$, AKT, p-EGFR $Tyr^{1086}$ and EGFR and a bar graph illustrating the percent inhibition of EGFR and phosphor-Akt in A-549 non small cell lung cancer xenografts by gefitinib and PX-866.
Figure 9:
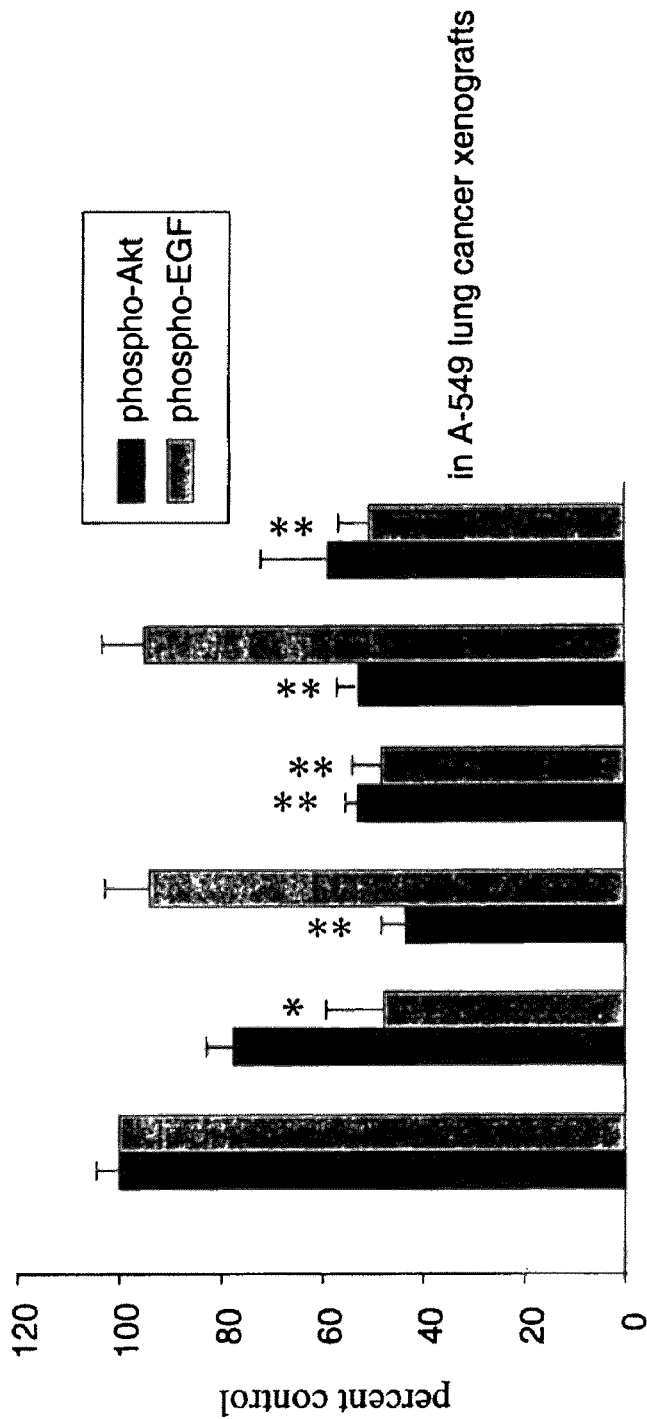
FIG. 9 is a bar graph of the percent control of phospho-Akt and phospho-EGFR in A549 lung cancer xenografts with administration of PX-866 alone (intravenously or orally) or gefitinib alone.

Inhibition of tumor EGFR and PtdIns-3-kinase signaling. Administration of gefitinib 75 mg/kg po to mice with A-549 tumor xenografts every other day for 5 days inhibited tumor phospho-EGFR by 43% but had no significant effect upon tumor phospho-Akt (FIG. 8). PX-866 12 mg/kg iv or 3 mg/kg po, every other day for 5 days, had no significant effect upon tumor phospho-EGFR but inhibited tumor phospho-Akt by 51% and 48%, respectively. The combination of gefitinib and PX-866 inhibited both tumor phospho-EGFR and tumor phospho-Akt. Similar effects were seen in a second study as depicted in FIG. 9. Thus, in A-549 tumor xenografts the EGFR and PtdIns-3-kinase pathways appear to function independently and to be selectively inhibited by gefitinib and PX-866, respectively.

Toxicity of long term PX-866 administration. The toxicity of long term administration of PX-866 to scid mice is summarized in Table 5. Values are the mean of 4 mice per group±SE.

TABLE 5

Toxicity of long term PX-866 Administration

| Treatment Group | ALT U/l | AST U/l | glucose mg/dl | WBC K/μl | Ne K/μl | LY K/μl |
|---|---|---|---|---|---|---|
| Control | 52.6 ± 13.6 | 142.9 ± 46.6 | 46.9 ± 5.1 | 8.9 ± 1.0 | 6.9 ± 0.8 | 1.1 ± 0.2 |
| PX-866 10 mg/Kg iv | 35.5 ± 11.7 | 105.2 ± 19.2 | 76.2 ± 3.6 | 14.6 ± 4.2 | 14.0 ± 2.7 | 1.8 ± 0.5 |
| PX-866 3 mg/Kg po | 47.6 ± 16.8 | 152.0 ± 47.2 | 113.5* ± 23.4 | 67.8* ± 19.7 | 53.6** ± 10.7 | 5.2 ± 3.9 |
| PX-866 1.5 mg/Kg po | 65.6 ± 27.5 | 140.5 ± 35.2 | 100.1** ± 10.9 | 16.6* ± 2.4 | 12.5* ± 1.9 | 3.1* ± 0.6 |

| Treatment Group | MO K/μl | RBC K/μl | Hb g/dl | Plt K/μl | Weight change g |
|---|---|---|---|---|---|
| Control | 0.8 ± 0.1 | 11.0 ± 0.3 | 15.4 ± 0.2 | 1427 ± 60 | 4.7 ± 0.3 |
| PX-866 10 mg/Kg iv | 1.1 ± 0.2 | 10.6 ± 0.0 | 14.4 ± 0.1 | 1390 ± 43 | 3.9* ± 0.2 |
| PX-866 3 mg/Kg po | 9.2 ± 3.6 | 10.4 ± 0.3 | 14.7 ± 0.4 | 1665 ± 227 | 1.3** ± 0.5 |
| PX-866 1.5 mg/Kg po | 1.8* ± 0.2 | 1030 ± 0.3 | 14.6 ± 0.3 | 1221* ± 18 | 3.9 ± 0.6 |

*p = <0.5,
**p < 0.01 compared to the control value

There was a decreased gain in body weight over the 4 weeks of treatment with PX-866 at 10 mg/kg iv and 3 mg/kg po, to 83% and 28% of the control weight gain, respectively (p 0.05). There was a significant increase in white blood cell counts following oral administration of PX-866, due primarily to increased blood neutrophil counts. All of the changes in body weight, plasma glucose and blood cell counts had returned to normal by 9 days after treatment stopped. The decrease in body weight and an increase in blood glucose were confirmed in two additional studies using scid mice, but the increase in blood cell counts was less pronounced in these studies (data not shown).

Figure 10:
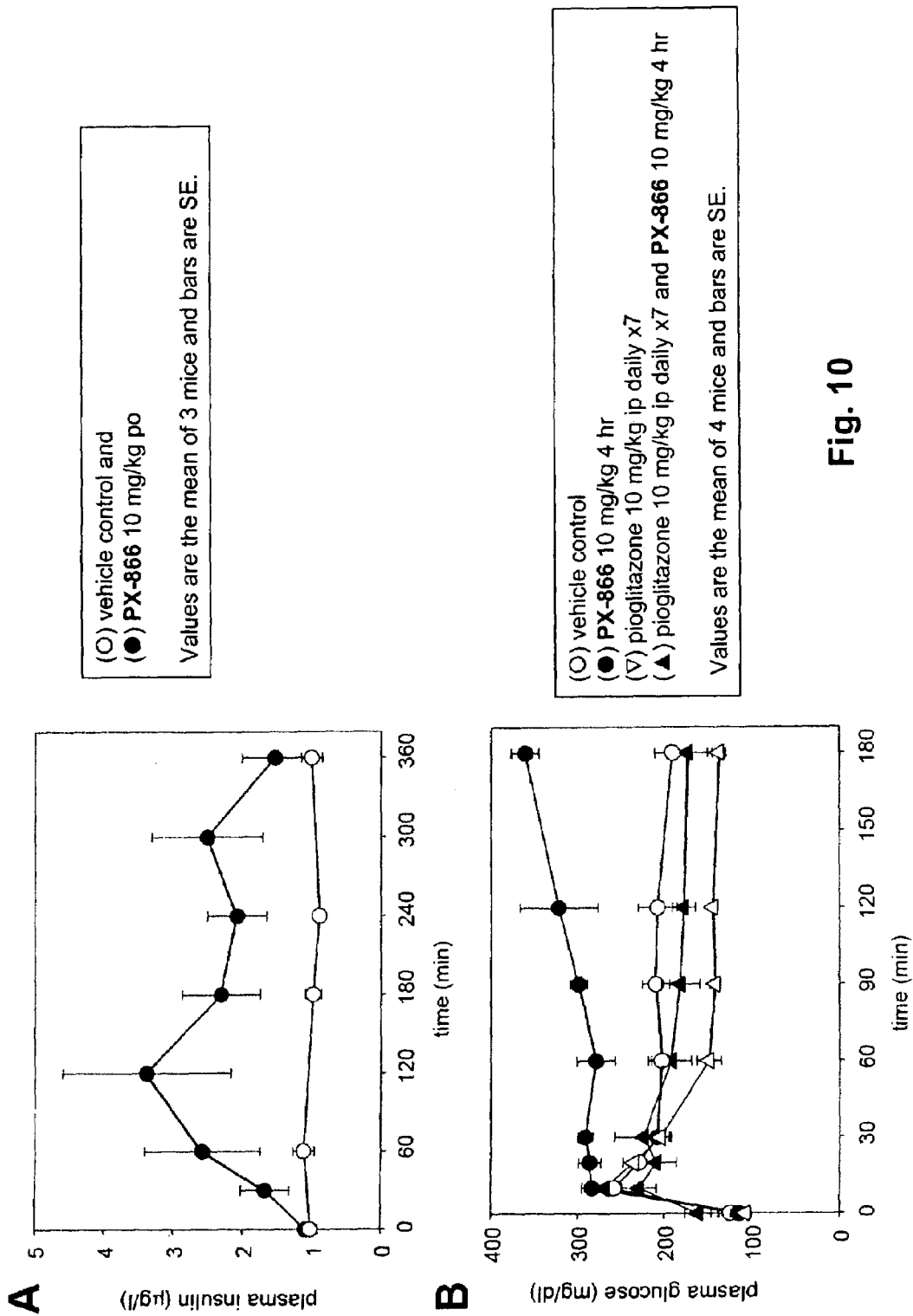
FIG. 10 is a graph depicting the effect of PX-866 on plasma insulin (A) and glucose tolerance (B).

PX-866 and glucose tolerance. In order to gain further insight into the mechanism for the increase in plasma glucose by PX-866, studies were conducted on insulin levels and on glucose tolerance following an oral dose of 1 g glucose/kg to fasted C57B1/6 mice (FIG. 10). Administration of PX-866 as a single dose of 10 mg/kg po caused an increase in plasma insulin levels for up to 5 hr. PX-866 also deceased glucose tolerance in the mice leading to an increase in plasma glucose, particularly at time points after 1 hr after glucose administration where plasma glucose was decreasing in non treated mice but increasing in the PX-866 treated mice. The results expressed as AUC 0-180 min for all the glucose tolerance studies are shown in Table 6, below. Values are the mean±SE of 4 mice per group.

TABLE 6

Effects of PX-866 on glucose tolerance in mice

| Treatment | $AUC_{0-180\ min}$ (mg · min · ml$^{-1}$) | $AUC_{0-180\ min}$ (mg · min · ml$^{-1}$) |
|---|---|---|
| PX-866 10 mg/kg po | | |
| No Drug | 369 ± 25 | 533 ± 17$^a$ |
| Insulin 0.075 μ/kg ip | 64 ± 25 | 64 ± 5 |
| Metformin 250 mg/kg IP QD × 5 | 367 ± 46 | 537 ± 4$^b$ |
| Pioglitazone 10 mg/kg ip QD × 7 | 274 ± 3 | 340 ± 39$^c$ |

TABLE 6-continued

Effects of PX-866 on glucose tolerance in mice

| Treatment | $AUC_{0-180\ min}$ (mg · min · ml$^{-1}$) | $AUC_{0-180\ min}$ (mg · min · ml$^{-1}$) |
|---|---|---|
| PX-866 3 mg/kg po QOD × 20 | | |
| | | 520 ± 14$^a$ |
| 8 day recovery | | 343 ± 14 |
| Pioglitazone 10 mg/kg IP QD × 7 | | 405 ± 26$^d$ |

$^a$p < 0.05 compared to untreated control
$^b$p < 0.05 compared to drug treated control without PX-866
$^c$p < 0.05 compared to PX-866 alone
$^d$p < 0.05 compared to chronic PX-866 alone Treatment with insulin at high doses overcame the increase in plasma glucose caused by PX-866 and significantly decreased the glucose $AUC_{0-180\ min}$ both control and PX-866 treated mice. The antihyperglycemic drug metformin had no effect upon the increase in blood glucose by PX-866, but the hypoglycemic thiazolidinedione drug pioglitazone almost completely blocked the increase (FIG. 10 and Table 6). Long term treatment with PX-866 at 9 mg/kg iv every other day for 15 doses gave an increase in nonfasting glucose levels (±S.E., n=4) from 133.7±16 mg/dl in control mice to 269.4±27.8 mg/dl (p<0.05) in the PX-866 treated mice. The treatment also gave an increase in plasma glucose $AUC_{0-180}$ min 24 hr after the last dose of PX-866, but this had recovered to control values 8 days after the last dose (Table 4). Pioglitazone significantly decreased the glucose $AUC_{0-120\ min}$ 24 hr after the last dose of long term PX-866 treatment to a value not significantly different to control (Table 4).

PX-866 and increased neutrophils. When PX-866 was administered to C57B1/6 mice at 3 mg/kg po every other day for 15 doses there was a significant increase in neutrophil counts (±S.E., n=4) from 1.2±0.3 K/:1 in control mice to 3.7±1.8 K/:1 in PX-866 treated mice (p<0.05), but with no significant change in any other blood elements. Bone marrow colony forming units showed no significant change in erythroid lineage CFU-GEMM, BFU-E or CFU-E and a small but significant decrease in myeloid CFU-GM (±S.E., n=4) from 388±52 colonies per 60,000 bone marrow cells plated in control mice to 168±59 colonies (p<0.05) in the PX-866 treated mice. At the same time there was an increase in the numbers of individual white cells in the cultures from PX-866 treated mice suggestive of altered cell adhesion.

Discussion. Sensitivity of nsc lung cancer cell lines to growth inhibition by gefitinib is associated with inhibition of EGF-stimulated EGFR autophosphorylation, down regulation of cell surface EGFR, ERK1/2 down regulation and inhibition of PtdIns-3-kinase/Akt signaling. The PtdIns-3-kinase/Akt pathway is a critical pathway for cancer cell survival. In a study by Ono et al gefitinib inhibited EGF-induced PtdIns-3-kinase/Akt signaling, as measured by phospho-Akt levels, in nearly all nsc lung cancer cell lines, however, only a few lines (3/11) showed inhibition of phospho-Akt under serum stimulated growth conditions. These results suggest that in many nsc lung cancer cell lines factors other than EGF are responsible for the activation of PtdIns-3-kinase/Akt signaling. Tumor cells with this phenotype may show limited responsiveness to the cytostatic and/or cytotoxic activities of EGFR inhibitors. Engelman et al have recently reported that ErbB-3 couples EGFR signaling to the activation of Ptdins-3-kinase/Akt, and that gefitinib inhibits phospho-Akt and cell growth only in nsc lung cancer cell lines expressing EGFR, either wild type or mutant, and ErbB-3. However, forced ErbB-3 expression did not render nsc lung cancer cells sensitive to gefitinib suggesting that pathways other than EGFR must activate the Ptdins-3-kinase/Akt signaling in ErbB-3 deficient cells. Other members of the ErbB receptor family may also couple with ErbB-3 to activate PtdIns-3-kinase and promote the cancer phenotype. We reasoned that inhibiting PtdIns-3-kinase could offer a rational strategy to potentiate the antitumor activity of gefitinib in gefitinib resistant nsc lung cancer cell lines.

For the present studies the A-549 nsc lung cancer cell line that is among the most resistant of nsc lung cancer lines to gefitinib and does not express ErbB-3 was chosen. PTEN deficiency can also render cells resistant to gefitinib growth inhibition presumably through constitutive activation of Ptdins-3-kinase/Akt signaling. However, genetic abnormalities of PTEN are relatively rare in lung cancer and A-549 cells, as do most nsc lung cancer cell lines, has wild type PTEN and non-constitutively activated levels of phospho-Akt. To inhibit PtdIns-3-kinase we used PX-866 that has been shown to down regulate tumor phospho-Akt and to exhibit antitumor activity in a number of human tumor xenograft models when administered either intravenously or orally.

It was found that PX-866 administered either iv or po inhibited the growth of A-549 nsc lung tumor xenografts in scid mice as effectively as gefitinib. Both agents appeared to be most active when administered long term giving tumor T/Cs around 50%. However, when PX-866 was administered together with gefitinib, A-549 tumor growth appeared to be held stationary during the first part of the treatment and increased only slightly during the later part of treatment. This was seen with both 100 mm3 tumors and with large advanced 600 mm3 tumors. Gefitinib failed to inhibit phospho-Akt in A-549 tumor xenografts. In the A-549 cell culture studies gefitinib also did not inhibit phospho-Akt cells under serum stimulated growth conditions and was only inhibitory in EGF-stimulated, serum deprived A-549 cells. In contrast, PX-866 inhibited phospho-Akt of A-549 cells under serum simulated growth conditions, and in A-549 human tumor xenografts. Gefitinib inhibited phospho-EGFR in the A-549 human tumor xenografts and PX-866 did not. Thus, PX-866 potentiated the antitumor activity of gefitinib against even very large A-549 tumor xenografts giving complete tumor growth control in the early stages of treatment. The inhibition of tumor growth was associated with inhibition of Ptdins-3-kinase/Akt signaling by PX-866 and was not observed with gefitinib alone.

A previous study has reported LY294002, a relatively toxic and non-specific PtdIns-3-kinase inhibitor with limited potential for clinical development, administered ip potentiates the antitumor activity of gefitinib against small, 6 to 100 mm3, U87:) EGFR human glioma cell xenografts that coexpress wild type and mutant tumor derived activated EGFR. In this study neither gefitinib nor LY294002 showed antitumor activity alone.

The major toxicity of prolonged administration of PX-866 was hyperglycemia and decreased glucose tolerance that reversed when drug administration was stopped. Insulin signals are relayed predominantly by the PtdIns-3-kinase isoform p110β but also by p110α while growth signals are relayed by PtdIns-3-kinase p110α. PX-866 is a more potent PtdIns-3-kinase p110α inhibitor than wortmannin but, unlike wortmannin, PX-866 is a poor inhibitor of inhibitor of PtdIns-3-kinase p110β. Acute administration of PX-866 to mice decreased glucose tolerance at the same time that plasma insulin levels were increased suggesting a decrease in sensitivity to insulin. This is similar to the phenotype of mice deficient in the Akt2 isoform that includes marked hyperglycemia, hyperinsulinemia and an impaired ability of insulin to lower blood glucose. In the present study a high dose of insulin was able to overcame the increase in blood glucose caused by PX-866. Metformin, a widely used drug for the treatment of hyperglycemia of type 2 diabetes, lowers blood glucose by stimulating AMP-activated proteinkinase (AMPK) downstream of PtdIns-3-kinase to increase fatty acid oxidation and to decrease triglyceride synthesis, hepatic glucose production and glucose utilization. AMPK mediates the stimulation of glucose uptake through translocation of the glucose transporter 4 (GLUT4) to the plasma membrane. It has been suggested that an AMPK activator such as metformin might enhance tumor cell survival if used with agents such as PtdIns-3-kinase or Akt inhibitors that impair glucose utilization. It was found that metformin had no effect on the decreased glucose tolerance caused by PX-866. It should be noted that a parallel pathway mediated by the recruitment of the Cbl proto-oncogene to the activated insulin receptor also increases glucose uptake by insulin.

In contrast to metformin, the thiazolidinedione hyperglycemic drug pioglitazone reversed the inhibitory effects of both acute and chronic PX-866 administration on glucose tolerance. Thiazolidenediones sensitize the body to the metabolic effects of insulin by acting as ligands for the peroxisome proliferator-activated receptor-(PPARγ) transcription factor that is present at high levels in adipose tissue. PPARγ also induces differentiation of tumor cells and PPARγ activation by pioglitazone has been reported to inhibit the growth of A-549 nsc lung tumor xenograft in scid mice. While all the details of insulin signaling through PtdIns-3-kinase and the effects of glucose lowering drugs such as metformin and pioglitazone remain to be elucidated, it appears that hyperglycemia caused by PtdIns-3-kinase inhibition by PX-866 is responsive to insulin and pioglitazone, which could be important for the clinical use of PX-866. The selectivity of PX-866 as an inhibitor of p110α relative to p110β, unlike wortmannin in which inhibits both p110α and p110β may also explain the more pronounced growth inhibitory effects of PX-866, and the ability of insulin and pioglitazone to reverse PX-866-induced hyperglycia.

The other pharmacological effect of PX-866 administration was an increase in circulating neutrophils at the same time there is a decrease in bone marrow CFU-GM colony formation The decrease in CFU-GM induced by PX-866 is consistent with the decreased sensitivity to granulocyte macrophage-colony stimulating factor (GM-CSF) observed in bone marrow derived macrophages of p85α−/− knockout mice. The increase in circulating neutrophils by PX-866 may reflect increased mobilization of progenitor cells into the peripheral circulation, perhaps associated with the decreased cell adhesion as seen in the p85α−/− knockout mice.

In summary, the Ptdins-3-kinase inhibitor PX-866 which shows selectivity for p110α compared to p110β would appear to potentiate the antitumor activity of the EGFR inhibitor gefitinib against even large A-549 nsc lung cancer xenografts, with substantially complete tumor growth control in the early stages of treatment. This therapeutic effect of PX-866 was associated with inhibition of tumor Akt phosphorylation which was not seen with gefitinib alone. The major toxicity of chronic PX-866 was a target-related hyperglycemia with a reversible decrease in glucose tolerance due to decreased sensitivity to insulin. The decreased glucose tolerance was insensitive to the AMPK inhibitor metformin but was reversed by insulin and the PPARγ activator pioglitazone. Long term PX-866 also caused increased neutrophils counts, apparently due to vascular mobilization. Thus, PX-866 by inhibiting PtdIns-3-kinase/Akt signaling, may have clinical utility in increasing the response to EGFR inhibitors such as gefitinib in patients with nsc lung cancer who do not respond to therapy with EGFR inhibitors.

EXAMPLE 11

Further studies of the effects of administration of PX-866 and gefitinib are illustrated below. The present example illustrates the effects of the combination of PX-866 and gefitinib (Iressa®) at higher doses. As shown in FIG. 11, PX-866 was administered 4 hours prior to Iressa® administration (See FIG. 11A) and 24 hours following gefitinib administration (See FIG. 11B) in A549 small cell lung xenografts. In addition, as shown in FIG. 12, PX-866 was also administered substantially simultaneously with gefitinib in A-549 small cell lun xenografts.

Antitumor activity of PX-866 with gefitinib in HT-29 colon cancer was also measured. As seen in FIG. 13, PX-866 increased the antitumor effect of gefitinib. Gefitinib was administered at 75 mg/kg po alone, PX-866 was administered orally at 2 mg/kg alone or 4 hours prior to gefitinib administration.

EXAMPLE 12

Figure 14:
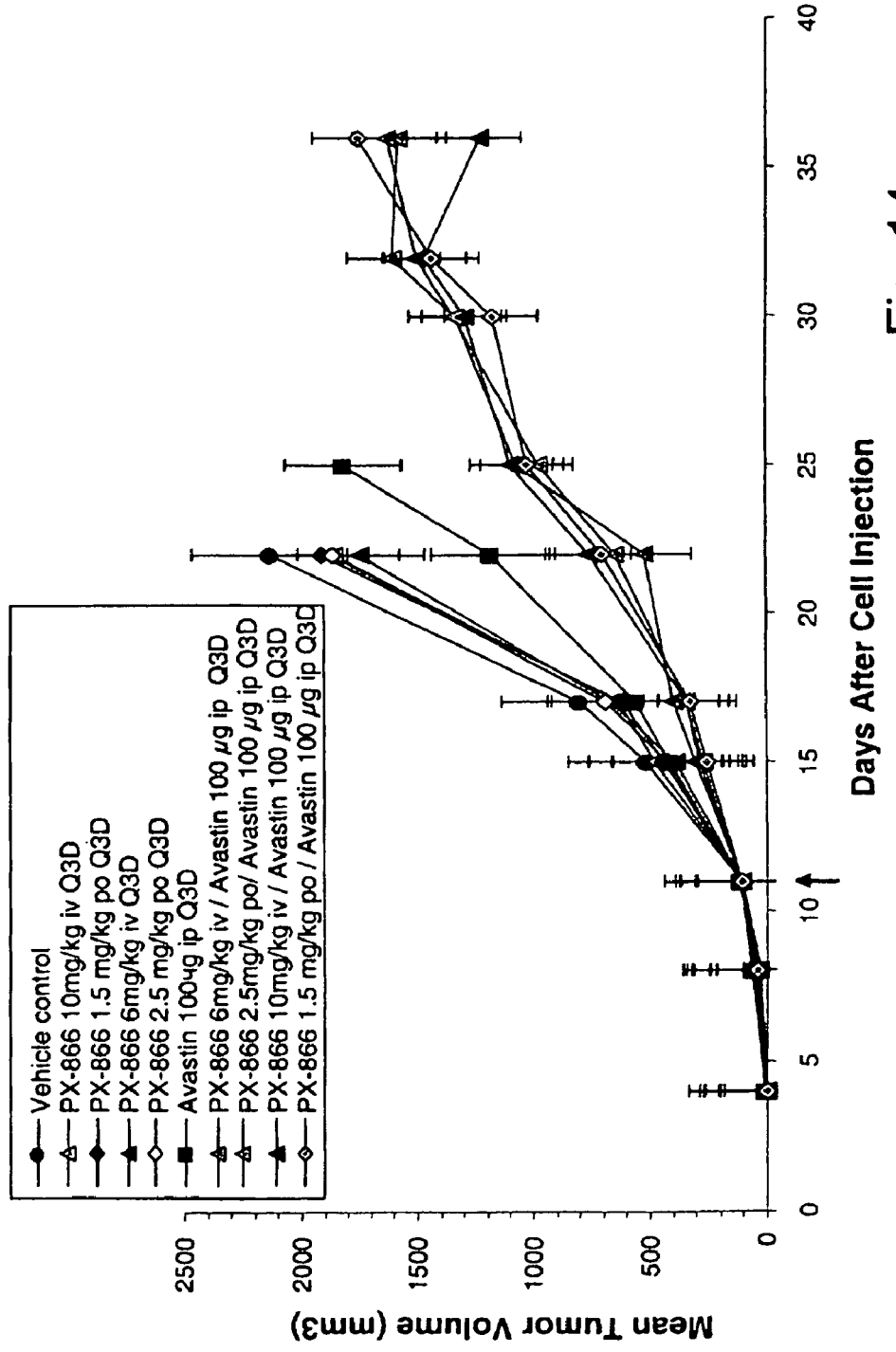
FIG. 14 is a graph of the mean tumor volume (in $mm^3$) following treatment with PX-866, a wortmannin analog of the present invention, alone or in combination with Avastin in A-673 thabdomyosarcom xenografts.

The antitumor effect of administration of PX-866 with bevacizumab (Avastin®) was measured. PX-866 was administered at varying doses intravenously or orally every three days alone or in combination with bevacizumab. As shown in FIG. 14, combination therapy significantly increased the antitumor activity of bevacizumab.

EXAMPLE 13

Figure 15:
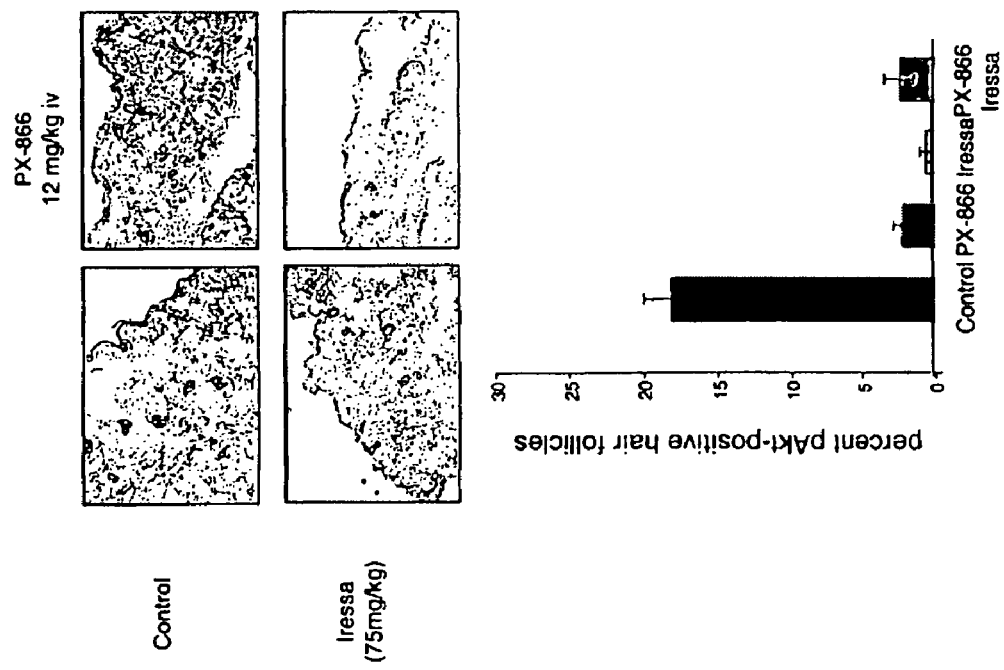
FIG. 15 is a bar graph depicting the percent of p-Akt-positive hair follicles in mouse skin following administration of PX-866, Iressa or a combination thereof and an immunohistochemistry depicting phosphor-Akt is inhibited by PX-866, Iressa or a combination thereof in mouse skin cells.

FIG. 15 depicts PX-866 inhibition of phosphor-Akt in mouse skin alone or in combination with gefitinib.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method of treating lung cancer comprising administering to a subject a pharmaceutically effective amount of a compound selected from

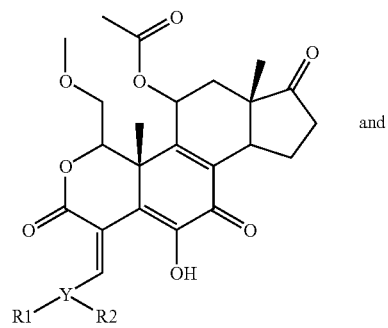

and

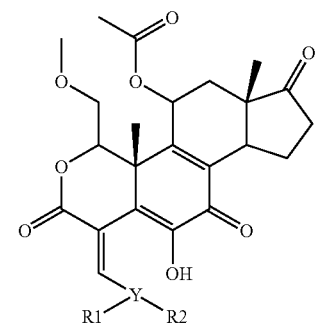

wherein Y is a heteroatom selected from nitrogen and sulfer and $R_1$ or $R_2$ are independently selected from an unsaturated alkyl, cyclic alkyl, or $R_1$ or $R_2$ together with Y form a heterocycle.

2. The method of claim 1, wherein said $R^1$ and $R^2$ are a unsaturated alkyl.

3. The method of claim 1, wherein said compound is administered orally.

4. The method of claim 1, wherein said compound is administered intravenously.
5. The method of claim 1, wherein said compound is:
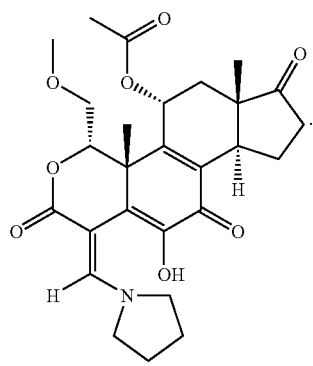
6. The method of claim 1, wherein said compound is:
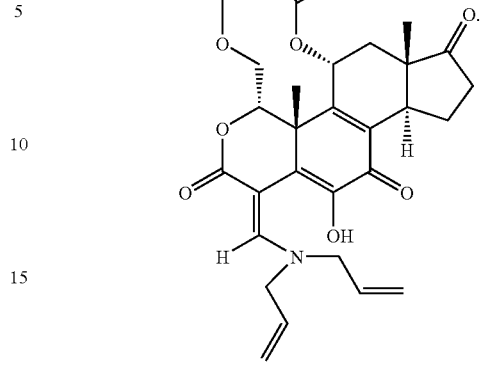
7. The method of claim 1, wherein the lung cancer is non small cell lung cancer.
8. The method of claim 1, wherein $R_1$ and $R_2$ together with Y form a heterocycle.
* * * * *

UNITED STATES PATENT AND TRADEMARK OFFICE
CERTIFICATE OF CORRECTION

PATENT NO. : 7,858,657 B2
APPLICATION NO. : 12/235730
DATED : December 28, 2010
INVENTOR(S) : Lynn D. Kirkpatrick et al.

It is certified that error appears in the above-identified patent and that said Letters Patent is hereby corrected as shown below:

On the title page, item (73), Assignees, replace

"Proix Pharmaceutical Corp., Seattle, WA (US)"

with:

-- Prolx Pharmaceutical Corp., Seattle, WA (US) --

Signed and Sealed this
Tenth Day of May, 2011

David J. Kappos
*Director of the United States Patent and Trademark Office*